US008450299B2

(12) United States Patent
Diliberti et al.

(10) Patent No.: US 8,450,299 B2
(45) Date of Patent: May 28, 2013

(54) METHODS OF HORMONAL TREATMENT UTILIZING ASCENDING-DOSE EXTENDED CYCLE REGIMENS

(75) Inventors: Charles E. Diliberti, Montclair, NJ (US); Kathleen Z. Reape, Bryn Mawr, PA (US); Lance J. Bronnenkant, Snyder, NY (US)

(73) Assignee: Teva Womans's Health, Inc., Woodcliff Lake, NJ (US)

( * ) Notice: Subject to any disclaimer, the term of this patent is extended or adjusted under 35 U.S.C. 154(b) by 0 days.

(21) Appl. No.: 13/492,138

(22) Filed: Jun. 8, 2012

(65) Prior Publication Data
US 2012/0252767 A1     Oct. 4, 2012

Related U.S. Application Data

(60) Division of application No. 11/892,026, filed on Aug. 17, 2007, which is a continuation of application No. 11/554,571, filed on Oct. 30, 2006, now abandoned, which is a continuation-in-part of application No. 11/245,471, filed on Oct. 7, 2005, now abandoned.

(60) Provisional application No. 60/684,568, filed on May 26, 2005, provisional application No. 60/616,424, filed on Oct. 7, 2004.

(51) Int. Cl.
*A61K 31/56*     (2006.01)

(52) U.S. Cl.
USPC ........... 514/170; 514/169; 514/178; 514/182; 514/841; 514/843

(58) Field of Classification Search
USPC .................. 154/170, 169, 178, 182, 841, 843
See application file for complete search history.

(56) References Cited

U.S. PATENT DOCUMENTS

| 3,414,119 | A | 12/1968 | Finch, Jr. |
|---|---|---|---|
| 3,568,828 | A | 3/1971 | Lerner |
| 4,145,416 | A | 3/1979 | Lachnit-Fixson et al. |
| 4,171,358 | A | 10/1979 | Black |
| 4,215,691 | A | 8/1980 | Wong |
| 4,291,014 | A | 9/1981 | Keith et al. |
| 4,292,315 | A | 9/1981 | Vorys |
| 4,390,531 | A | 6/1983 | Edgren |
| 4,438,139 | A | 3/1984 | Keith et al. |
| 4,530,839 | A | 7/1985 | Pasquale |
| 4,534,468 | A | 8/1985 | Nuckols et al. |
| 4,544,554 | A | 10/1985 | Pasquale |
| 4,616,006 | A | 10/1986 | Pasquale |
| 4,628,051 | A | 12/1986 | Pasquale |
| 4,685,911 | A | 8/1987 | Konno et al. |
| 4,736,849 | A | 4/1988 | Leonard et al. |
| 4,752,478 | A | 6/1988 | Bondi et al. |
| 4,758,592 | A | 7/1988 | Horrobin et al. |
| 4,762,717 | A | 8/1988 | Crowley, Jr. |
| 4,826,831 | A | 5/1989 | Plunkett et al. |
| 4,848,585 | A | 7/1989 | Snyder |
| 4,962,098 | A | 10/1990 | Boissonneault |
| 4,971,998 | A | 11/1990 | Wurtman et al. |
| 4,994,449 | A | 2/1991 | Leonard |
| 4,998,623 | A | 3/1991 | Doull |
| 5,010,070 | A | 4/1991 | Boissonneault |
| 5,043,331 | A | 8/1991 | Hirvonen et al. |
| 5,098,714 | A | 3/1992 | Wright et al. |
| 5,105,949 | A | 4/1992 | Blair |
| 5,108,995 | A | 4/1992 | Casper |
| 5,208,225 | A | 5/1993 | Boissonneault et al. |
| D339,742 | S | 9/1993 | Walchek, Jr. et al. |
| 5,256,421 | A | 10/1993 | Casper |
| D340,860 | S | 11/1993 | Gordon et al. |
| 5,262,408 | A | 11/1993 | Bergink |
| 5,276,022 | A | 1/1994 | Casper |
| 5,280,023 | A | 1/1994 | Ehrlich et al. |
| 5,296,230 | A | 3/1994 | Chien et al. |
| 5,340,584 | A | 8/1994 | Spicer et al. |
| 5,348,158 | A | 9/1994 | Honan |
| 5,351,818 | A | 10/1994 | Daneshvar |
| 5,368,187 | A | 11/1994 | Poncetta et al. |
| 5,372,258 | A | 12/1994 | Daneshvar |
| 5,382,573 | A | 1/1995 | Casper |
| D358,546 | S | 5/1995 | Walchek, Jr. et al. |
| D358,762 | S | 5/1995 | Walchek, Jr. et al. |

(Continued)

FOREIGN PATENT DOCUMENTS

| CA | 2140011 A1 | 1/1994 |
|---|---|---|
| CA | 2179728 | 6/1995 |

(Continued)

OTHER PUBLICATIONS

Anderson et al., "A multicenter, randomized study of extended cycle oral contraceptive," Contraception (Aug. 2003) 68: pp. 89-96.*
Leyden et al., "Efficacy of a low-dose oral contraceptive containing 20 µg of ethinyl estradiol and 100 µg of levonorgestrel for the treatment of moderate acne: A randomized, placebo controlled trial," J. Am. Acad. Dermatol., 2002; 47: pp. 399-409.*
Anderson, F.D., et al., "A multicenter, randomized study of an extended cycle oral contraceptive," Contraception 68:89-96, Elsevier (Aug. 2003).
Hamerlynck, J.V., et al., "Postponement of Withdrawal Bleeding in Women Using Low-Dose Combined Oral Contraceptives," Contraception 35:199-205, Elsevier Inc. (1987).
Kornaat, H., et al., "The Acceptance of a 7-Week Cycle with a Modern Low-Dose Oral Contraceptive (Minulet®)," Contraception 45:119-127, Elsevier Inc. (1992).
Leyden, J., et al., "Efficacy of a low-dose oral contraceptive containing 20 µg of ethinyl estradiol and 100 µg of levonorgestrel for the treatment of moderate acne: A randomized, placebo-controlled trial," J. Am. Acad. Dermatol. 47:399-409, Mosby (Sep. 2002).

(Continued)

*Primary Examiner* — Sreeni Padmanabhan
*Assistant Examiner* — Jody Karol
(74) *Attorney, Agent, or Firm* — Sterne, Kessler, Goldstein & Fox, P.L.L.C.

(57) ABSTRACT

The present invention provides ascending-dose extended cycle regimens in which a female is administered an estrogen and a progestin for a period of greater than 30 or 31 consecutive days, optionally followed by a hormone-free period or by a period of administration of estrogen. The disclosed regimens can be administered to a female to provide contraceptive and non-contraceptive benefits.

20 Claims, No Drawings

U.S. PATENT DOCUMENTS

| | | | |
|---|---|---|---|
| 5,510,341 A | 4/1996 | Ehrlich et al. | |
| 5,552,394 A | 9/1996 | Hodgen | |
| 5,567,695 A | 10/1996 | Labrie | |
| 5,585,370 A | 12/1996 | Casper | |
| 5,633,242 A | 5/1997 | Oettel et al. | |
| 5,662,927 A | 9/1997 | Ehrlich et al. | |
| RE35,724 E | 2/1998 | Pasquale | |
| 5,747,480 A * | 5/1998 | Gast | 514/179 |
| 5,753,639 A | 5/1998 | Labrie | |
| 5,756,490 A | 5/1998 | Lachnit et al. | |
| 5,827,843 A | 10/1998 | Koninckx | |
| 5,858,405 A | 1/1999 | Gast | |
| 5,891,867 A | 4/1999 | Lanquetin et al. | |
| 5,898,032 A | 4/1999 | Hodgen | |
| D411,445 S | 6/1999 | Anderson | |
| RE36,247 E | 7/1999 | Plunkett et al. | |
| D414,106 S | 9/1999 | Anderson | |
| 5,980,940 A | 11/1999 | Spona et al. | |
| 6,027,749 A | 2/2000 | Schmidt-Gollwitzer et al. | |
| 6,028,064 A | 2/2000 | Rodriguez et al. | |
| 6,036,018 A | 3/2000 | Harrold | |
| 6,039,208 A | 3/2000 | Lambelet, Jr. | |
| D423,111 S | 4/2000 | Davis et al. | |
| D430,392 S | 9/2000 | Noble | |
| 6,139,873 A | 10/2000 | Hughes, Jr. et al. | |
| 6,156,742 A | 12/2000 | Mackenzie | |
| 6,173,838 B1 | 1/2001 | Brozell | |
| 6,199,689 B1 | 3/2001 | Higuchi et al. | |
| 6,214,815 B1 | 4/2001 | Shangold et al. | |
| 6,219,997 B1 | 4/2001 | Friberg et al. | |
| 6,251,956 B1 | 6/2001 | Kafrissen et al. | |
| 6,265,393 B1 | 7/2001 | Heinrichs | |
| 6,306,914 B1 | 10/2001 | de Ziegler et al. | |
| 6,310,054 B1 | 10/2001 | Rodriguez | |
| 6,312,722 B1 | 11/2001 | Schmidt-Gollwitzer et al. | |
| 6,319,911 B1 | 11/2001 | Rodriguez | |
| 6,338,408 B1 | 1/2002 | Anderson | |
| D460,254 S | 7/2002 | Rufo | |
| RE37,838 E | 9/2002 | Spona et al. | |
| 6,451,779 B1 | 9/2002 | Hesch | |
| 6,479,475 B1 | 11/2002 | Gast | |
| 6,500,814 B1 | 12/2002 | Hesch | |
| 6,511,970 B1 | 1/2003 | Rodriguez | |
| 6,550,618 B2 | 4/2003 | Peterson | |
| 6,569,857 B1 | 5/2003 | Hermelin et al. | |
| 6,667,050 B1 | 12/2003 | Boissonneault et al. | |
| 6,765,002 B2 | 7/2004 | Rodriguez | |
| 6,787,531 B1 | 9/2004 | Hilman et al. | |
| 6,789,677 B2 | 9/2004 | Maietta | |
| D508,164 S | 8/2005 | Coe et al. | |
| 7,150,355 B2 | 12/2006 | Coe et al. | |
| RE39,861 E | 9/2007 | Hodgen | |
| 7,297,688 B2 | 11/2007 | Grubb | |
| 7,320,969 B2 | 1/2008 | Bell et al. | |
| 7,427,609 B2 | 9/2008 | Leonard et al. | |
| 7,615,545 B2 | 11/2009 | Bell et al. | |
| 7,772,219 B2 | 8/2010 | Ben-Maimon et al. | |
| 7,855,190 B2 | 12/2010 | Bell et al. | |
| 7,858,605 B2 | 12/2010 | Bell et al. | |
| 7,942,267 B2 | 5/2011 | Coe et al. | |
| 2001/0020015 A1 | 9/2001 | Kafrissen et al. | |
| 2001/0044431 A1 | 11/2001 | Rodriguez | |
| 2002/0132801 A1 | 9/2002 | Heil et al. | |
| 2002/0169205 A1 | 11/2002 | Chwalisz et al. | |
| 2002/0193356 A1* | 12/2002 | Van Beek et al. | 514/169 |
| 2003/0018018 A1 | 1/2003 | Hodgen et al. | |
| 2003/0106814 A1 | 6/2003 | Gelardi et al. | |
| 2003/0114429 A1 | 6/2003 | Hilman et al. | |
| 2003/0119798 A1 | 6/2003 | Heil et al. | |
| 2003/0139381 A1* | 7/2003 | Bell et al. | 514/170 |
| 2003/0144258 A1 | 7/2003 | Heil et al. | |
| 2003/0216366 A1 | 11/2003 | Leonard et al. | |
| 2003/0219471 A1 | 11/2003 | Caubel et al. | |
| 2003/0229057 A1 | 12/2003 | Caubel et al. | |
| 2004/0009960 A1 | 1/2004 | Heil et al. | |
| 2004/0142914 A1 | 7/2004 | Friedman et al. | |
| 2004/0220152 A1 | 11/2004 | Ben-Maimon et al. | |
| 2004/0222123 A1 | 11/2004 | Niemann | |
| 2004/0251301 A1 | 12/2004 | Niemann et al. | |
| 2005/0038006 A1 | 2/2005 | Shangold et al. | |
| 2005/0051454 A1 | 3/2005 | Coe et al. | |
| 2005/0064031 A1 | 3/2005 | Stockermann et al. | |
| 2005/0090475 A1* | 4/2005 | LaGuardia | 514/170 |
| 2005/0113350 A1 | 5/2005 | Duesterberg et al. | |
| 2005/0143359 A1* | 6/2005 | Bell et al. | 514/170 |
| 2005/0227952 A1 | 10/2005 | Boissonneault | |
| 2005/0250747 A1 | 11/2005 | Sachse | |
| 2005/0272712 A1 | 12/2005 | Grubb et al. | |
| 2006/0135496 A1 | 6/2006 | DiLiberti et al. | |
| 2007/0111975 A1 | 5/2007 | DiLiberti et al. | |
| 2007/0158233 A1 | 7/2007 | Coe et al. | |
| 2007/0207945 A1 | 9/2007 | Ellman | |
| 2008/0064670 A1 | 3/2008 | Bell et al. | |
| 2008/0132473 A1 | 6/2008 | Bell et al. | |
| 2008/0234240 A1 | 9/2008 | Düsterberg et al. | |
| 2009/0163454 A1 | 6/2009 | Hait et al. | |
| 2009/0247493 A1 | 10/2009 | DiLiberti et al. | |
| 2010/0298279 A1 | 11/2010 | Bell et al. | |
| 2011/0124611 A1 | 5/2011 | Bell et al. | |

FOREIGN PATENT DOCUMENTS

| | | |
|---|---|---|
| CA | 2186739 | 10/1995 |
| CA | 2217564 | 10/1996 |
| CA | 2189907 A1 | 5/1997 |
| CA | 2301162 A1 | 3/1999 |
| CA | 2468748 A1 | 6/2003 |
| CA | 2524474 A1 | 11/2004 |
| CN | 1159161 | 9/1997 |
| CN | 1 189 101 A | 7/1998 |
| DE | 19525017 A1 | 1/1997 |
| EP | 0 253 607 A1 | 1/1988 |
| EP | 0 911 029 B1 | 4/1999 |
| JP | H03-500884 | 5/1989 |
| JP | H5-58909 | 9/1993 |
| JP | H7-58909 A | 3/1995 |
| JP | H9-502733 | 3/1997 |
| JP | H9-511243 A | 11/1997 |
| JP | H11-29481 | 2/1999 |
| NZ | 555299 | 10/2008 |
| NZ | 545130 | 3/2009 |
| NZ | 519627 | 3/2011 |
| NZ | 570295 | 5/2011 |
| NZ | 574964 | 10/2011 |
| NZ | 585546 | 10/2011 |
| WO | WO 89/03692 | 5/1989 |
| WO | WO 93/17686 A1 | 9/1993 |
| WO | WO 94/02103 | 2/1994 |
| WO | WO 97/01342 | 1/1997 |
| WO | WO 97/06807 A2 | 2/1997 |
| WO | WO 98/04246 A2 | 2/1998 |
| WO | WO 98/04266 A1 | 2/1998 |
| WO | WO 98/04267 A1 | 2/1998 |
| WO | WO 00/38691 A1 | 7/2000 |
| WO | WO 01/93848 A2 | 12/2001 |
| WO | WO 02/03975 A2 | 1/2002 |
| WO | WO 03/049744 A1 | 6/2003 |
| WO | WO 2004/080442 A1 | 9/2004 |
| WO | WO 2004/098517 A2 | 11/2004 |
| WO | WO 2005/007112 A2 | 1/2005 |
| WO | WO 2005/032558 A1 | 4/2005 |
| WO | WO 2005/092346 | 10/2005 |
| WO | WO 2006/042021 A2 | 4/2006 |

OTHER PUBLICATIONS

Miller, L., and Notter, K.M., "Menstrual Reduction with Extended Use of Combination Oral Contraceptive Pills: Randomized Controlled Trial," *Obstet. Gynecol.* 98:771-778, Elsevier Science, Inc. (2001).

International Search Report for International Application No. PCT/US2005/035997, mailed Apr. 7, 2006, European Patent Office, Rijswijk, The Netherlands.

Written Opinion for International Application No. PCT/US2005/035997, received Apr. 7, 2006, european Patent Office, Munich, Germany.

International Search Report for International Application No. PCT/US2007/022832, mailed Sep. 18, 2008, United States Patent Office, Alexandria, Virginia.

Written Opinion for International Application No. PCT/US2007/022832, mailed Sep. 18, 2008, United States Patnet Office, Alexandria, Virginia.

Hillard, P.J., "Oral contraception noncompliance: The extent of the problem," *Adv. Contracep. 8(Suppl. 1)*:13-20, Kluwer Academic Publishers, Netherlands (1992).

American Psychiatric Association, "Premenstrual Dysphoric Disorder," in DSM-IV™:Diagnostic and Statistical Manual of Mental Disorders, pp. 715-718, 4th edition, American Psychiatric Association, Washington, DC, United States (1994).

Anderson, F., "The Safety and Efficacy of Seasonale, a Novel 91-Day Extended Oral Contraceptive Regimen," *Obstet. Gynecol.* 99:26S, Lippincott Williams & Wilkins, United States (2002).

Anderson, F., et al., "Endometrial effects of a 91-day extended-regimen oral contraceptive with low-dose estrogen in place of placebo," *Contraception* 77:91-96, Elsevier, United States (2008).

Anderson, F., et al., "Endometrial microstructure after long-term use of a 91-day extended-cycle oral contraceptive regimen," *Contraception* 71:55-59, Elsevier, United States (2005).

Anderson, F., et al., "Long-term safety of an extended-cycle oral contraceptive (Seasonale): a 2-year multicenter open-label extension trial," *Am. J. Obstet. Gynecol.* 195:92-96, Elsevier, United States (2006).

Anderson, F., et al., "Safety and efficacy of an extended-regimen oral contraceptive utilizing continuous low-dose ethinyl estradiol," *Contraception* 73:229-234, Elsevier, United States (2006).

Branigan, E. and Estes, M., "A randomized clinical trial of treatment of clomiphene citrate-resistant anovulation with the use of oral contraceptive pill suppression and repeat clomiphene citrate treatment," *Am. J. Obstet. Gynecol.* 188:1424-1430, Elsevier, United States (Jun. 2003).

Branigan, E. and Estes, M., "Treatment of chronic anovulation resistant to clomiphene citrate (CC) by using oral contraceptive ovarian suppression followed by repeat CC treatment," *Fertil. Steril.* 71:544-546, Hoeber, United States (1999).

Brunner Huber, L., et al., "Obesity and Oral Contraceptive Failure," *Am. J. Epidemiol.* 166: 1306-1311, Oxford University Press, United States (2007).

Budavari, S., ed., "4112. Fluoxetine," in *Merck Index*, p. 655, 11th Ed., Merck & Company, Inc., Whitehouse Station, NJ, United States (1989).

Cachrimanidou, A., et al., "Long-interval treatment regimen with a desogestrel-containing oral contraceptive," *Contraception* 48:205-216, Butterworth-Heinemann (1993).

Case, A. and Reid, R., "Effects of the Menstrual Cycle on Medical Disorders," *Arch. Intern. Med.* 158:1405-1412, American Medical Association, United States (1998).

Coffee, A., "Hormone-Based Contraception: The Extended Cycle Regimen," Supplement to Drug Topics, pp. 3-15, Advanstar Communications, Inc. (Jan. 2004).

Comparison of Seasonale with other birth control products, Market data from Jun. 2001-Jan. 2004, IMS Health, United States, 4 pages.

Buechner, M., et al., "Coolest Inventions: Coolest Inventions 2003," Time Magazine US, Nov. 17, 2003 issue, 26 pages (Nov. 2003).

Daugherty, J., "Treatment Strategies for Premenstrual Syndrome," *Am. Fam. Phys.* 58:183-192, American Academy of Family Physicians, United States (1998).

Davies, G., et al., "Ovarian Activity and Bleeding Patterns During Extended Continuous Use of a Combined Contraceptive Vaginal Ring," *Contraception* 46:269-278, Elsevier, United States (1992).

Davis, M., "Evaluation of the Long-Term Safety of a 91-Day Extended Regiment Oral Contraceptive with Low-dose Estrogen in Place of Placebo," Abstract P42, *Contraception* 76:157-178, Elsevier, United States (2007).

de Voogd, W., "Postponement of Withdrawal Bleeding With a Monophasic Oral Contraceptive Containing Desogestrel and Ethinylestradiol," *Contraception* 44:107-112, Elsevier, United States (1991).

Dennerstein, L., et al., "Headache and Sex Hormone Therapy," *Headache* 18:146-152, Wiley, United States (1978).

Dickey, R., "Oral Contracepton: Realizing the Promise by Overcoming the Pitfalls," Individualizing Oral Contraceptive Therapy, OBG Management Supplement, pp. 2-6, Watson Pharma, Inc., United States (Oct. 2000).

Drug Monograph for Cyclessa, Center for Drug Evaluation and Research, Application No. 21-090, NDA (2000).

Drug Monograph for Desogen, Epocrates Online, Accessed at https://online.epocrates.com/noFrame/monographPrintAction.do, Accessed on Aug. 9, 2012.

Drug Monograph for Desogestrel, U.S. Food & Drug Administration, Accessed at http://www.accessdata.fda.gov/drugsatfda_docs/anda/99/075256_desogestrel_toc.cfm, Last updated on Jul. 29, 2003, Accessed on Aug. 9, 2012.

Drug Monograph for Kariva, Epocrates Online, Accessed at https://online.epocrates.com/u/10a2688/Kariva, Accessed on Aug. 9, 2012.

Drug Monograph for Mircette. Epocrates Online, Accessed at https://online.epocrates.com/u/10a981/Mircette, Accessed on Aug. 9, 2012.

Drug Monograph for Ortho-Cept, Accessed at https://online.epocrates.com/noFrame/monographPrintAction.do, Accessed on Aug. 9, 2012.

*Duramed Pharmaceuticals, Inc.* v. *Sandoz Inc.*, Civil Docket Case #: 3:07-cv-05940-MLC-TJB, U.S. District Court, District of New Jersey (Trenton), Filed on Dec. 13, 2007, 16 pages.

*Duramed Pharmaceuticals, Inc.* v. *Sandoz Inc.*, et al., Civil Docket Case #: 3:07-cv-05940-MLC-TJB, U.S. District Court, District of New Jersey (Trenton), "Defendant Sandoz Inc.'s Amended Answer, Affirmative Defenses and Counterclaims to Plaintiff's Complaint," Filed on Sep. 25, 2008, 19 pages.

*Duramed Pharmaceuticals, Inc.* v. *Watson Laboratories, Inc.* et al., Civil Docket Case #: 3:08-cv-00116-LRH-RAM, U.S. District Court, District of Nevada (Reno), Filed on Mar. 6, 2008, 24 pages.

*Duramed Pharmaceuticals, Inc.* v. *Watson Laboratories, Inc.*, Civil Docket Case #: 3:08-cv-00116 (LRH-RAM), U.S. District Court, District of Nevada (Reno), "First Amended Answer, Affirmative Defenses and Counterclaims of Defendant Watson Laboratories, Inc. ," Filed on Dec. 19, 2008, 12 pages.

*Duramed Pharmaceuticals, Inc.* v. *Watson Pharma, Inc.* et al., Civil Docket Case #: 3:07-cv-05941-MLC-TJB, U.S. District Court, District of New Jersey (Trenton), Filed on Dec. 13, 2007, 19 pages.

*Duramed Pharmaceuticals, Inc.* v. *Watson Pharma, Inc.*, et al., Civil Docket Case #:3:07-cv-05941-MLC-TJB, U.S. District Court, District of New Jersey (Trenton), "Answer and Counterclaims of Defendants/Counterclaim-Plaintiffs Watson Pharma, Inc., Watson Laboratories, Inc., and Watson Pharmaceuticals, Inc.," filed on Mar. 3, 2008, 28 pages.

Düsterberg, B., et al., "Half-lives in Plasma and Bioavailability of Ethinylestradiol in Laboratory Animals," *Arzneimittelforschung (Drug Res.)* 36:1187-1190, Edititio Cantor, Canada (1986).

Düsterberg, B., et al., "Terminal Half-lives in Plasma and Bioavailability of Norethisterone, Levonorgestrel, Cyproterone acetate and Gestodene in Rats, Beagles and Rhesus Monkeys," *Contraception* 24:673-383, Elsevier, Untied States (1981).

Facts and Comparisons, Chapter 3, pp. 108b-108e, 1985 (Best Available Copy).

Fernandez, E., et al., "Oral contraceptives and colorectal cancer risk: a meta-analysis," *Brit. J. Canc.* 84:722-727, Cancer Research Campaign, United Kingdom (2001).

Frackiewicz, E. and Shiovitz, T., "Evaluation and Management of Premenstrual Syndrome and Premenstrual Dysphoric Disorder," *J. Am. Pharm. Assoc.* 41:437-447, American Pharmaceutical Association, United States (2001).

Freeman, E., et al., "Concurrent Use of Oral Contraceptives With Antidepressants for Premenstrual Syndromes," *J. Clin. Psychopharmacol.* 21:540-542, Williams & Wilkins, United States (2001).

Freeman, E., et al., "Evaluation of a unique oral contraceptive in the treatment of premenstrual dysphoric disorder," *J. Womens Health Gend. Based Med.* 10:561-569, Mary Ann Liebert, Inc., United States (2001).

Garraway, W., et al., "Limb Fractures in a Defined Population. I. Frequency and Distribution," *Mayo Clin. Proc.* 54:701-707, Mayo Clinic, United States (1979).

Gitsch, E., et al., "Estrogen-progestogen treatment enhances the ovulatory response to clomiphene in amenorrheic patients," *Fertil. Steril.* 29:159-163, Elsevier for the American Society for Reproductive Medicine, United States (1978).

Glaser, J., "Seasonale®, Market Research," carried out by Ziment Associates on behalf of Barr Laboratories, Inc., 14 pages, Israel (Jan. 2003).

Goldzieher, J., "Use and Misuse of the Term Potency with Respect to Oral contraceptives," *J. Reproductive Med.* 31:533-539, The Journal of Reproductive Medicine, Inc., United States (1986).

Graham, C., and Sherwin, B., "A prospective treatment study of premenstrual symptoms using a triphasic oral contraceptive," *J. Psychosom. Res.* 36:257-266, Pergamon Press, United Kingdom (1992).

Guillebaud, J., ed., "Contraception. Your questions answered," 5$^{th}$ ed., pp. 75, 131, 154-155, Churchill Livingstone, New York, NY, United States (1986).

Gusberg, S. and Hall, R., "Precursors of Corpus Cancer. III. The Appearance of Cancer of the Endometrium in Estrogenically Conditioned Patients," *Obstet. Gynecol.* 17:397-412, Paul B. Hoeber, Inc., Lippincott Williams & Wilkins, United States (1961).

"Headaches: OCs are 'guilty by associatin'," *Contracept. Technol. Update* 14:109-112, Thomson American Health Consultants, United States (1993).

Hipkin, L., Col., "The Induction of Amenorrhoea," *J.R. Army Med. Corps* 138:15-18, Royal Army Medical Corps, Regimental Headquarters, United States (1992).

Holt. V., et al., "Body Mass Index, Weight, and Oral Contraceptive Failure Risk," *Obstet. Gynecol.* 105:46-52, Lippincott Williams & Wilkins, United States (2005).

Holt, V., et al., "Body Weight and Risk of Oral Contraceptive Failure," Obstet. Gynecol. 99:820-827, American College of Obstetricians and Gynecologists, United States (May 2002).

Katzung, B., ed., "Hormonal Contraception," in *Basic & Clinical Pharmacology*, pp. 619-623, 6th ed., Appleton & Lange, Norwalk, CT, Untied States (1995).

Kaunitz, A Randomized Trial to Evaluate the Efficacy and Safety of a Low Dose Extended-Cycle Oral Contraceptive, Seasonale Lo,38 [Poster] American College of Obstetricians and Gynecologists (ACOG), 45$^{th}$ Annual Clinical Ob/Gyn Meeting, May 6-10, 2006, Washington, D.C., United States.

Kay, C. and Wingrave, S., "Oral Contraceptives and Rheumatoid Arthritis," *Lancet* 1:1437, Lancet Publishing Group, United Kingdom (1983).

Killick, S., et al., "Ovarian activity in women taking an oral contraceptive containing 20 ug ethinyl estradiol and 150 ug desogestrel: Effects of low estrogen doses during the hormone-free interval," *Am. J. Obstet. Gynecol.* 179:S18-S24, Mosby, Inc., United States (1998).

King, R., and Whitehead, M., "Assessment of the potency of orally administered.progestins in women," *Fertil. Steril.* 46:1062-1066, Elsevier for the American Society for Reproductive Medicine, United States (1986).

Kistner, R., "Current Status of the Hormonal Treatment of Endometriosis," *Clin. Obstet. Gynecol.* 9:271-292, Harper & Row, Publishers, Inc., United States (1966).

Kistner, R., "Management of Endometriosis in the Infertile Patient," *Fertil. Steril.* 26:1151-1166, Harper & Row, Publishers, Inc., United States (1975).

Kistner, R., "The Effects of New Synthetic Progestogens on Endometriosis in the Human Female," *Fertil. Steril.* 16:61-80, Harper & Row, Publishers, Inc., United States (1965).

Kistner, R., "The Treatment of Endometriosis by Inducing Pseudopregnancy with Ovarian Hormones," *Fertil. Steril.* 10:539-556, Paul B. Hoeber, Inc. Publishers, United States (1959).

Koetsawang, S., et al., "A Randomized, Double-Blind Study of Six Combined Oral Contraceptives," Contraception 25:231-241, Elsevier, United States (1982).

Kousta, E., et al., "Modern use of clomiphene citrate in induction of ovulation," *Hum. Reprod. Update* 3:359-365, Published for the European Society of Human Reproduction and Embryology by Oxford University Press, United States (1997).

Kovacs, G., et al., "A trimonthly regimen for oral contraceptives," *Br. J. Fam. Plann.* 19:274-275, Faculty of Family Planning and Reproductive Health Care of the Royal College of Obstetricians and Gynaecologists, United States (1994).

Kudrow, L., "The Relationship of Headache Frequency to Hormone Use in Migraine," *Headache* 15:36-40, American Association for the Study of Headache, United States (1975).

Kuhl, H., "Comparative Pharmacology of Newer Progestogens," *Drugs* 51:189-215, ADIS International Ltd., ADIS Press, United States (1996).

Küpper, C., and Loch, E., "Prämenstruelles Syndrom," *Deutsche Apotheker Zeitung* 136:23-29, Deutcher Apotheker Verlag, Germany (1996).

Linos, A., et al., "Rheumatoid Arthritis and Oral Contraceptives," *Lancet* 1:871, The Lancet Publishing Group, United Kingdom (1978).

Loudon, N., et al., "Acceptability of an oral contraceptive that reduces the frequency of menstruation: the tri-cycle pill regimen," *Br. Med. J.* 2:487-490, British Medical Association, United Kingdom (1977).

Lundeen, S., et al., "Rat uterine complement C3 expression as a model for progesterone receptor modulators: characterization of the new progestin trimegestone," J. Steroid Biochem. Mol.. Biol. 78:137-143, Elsevier Science Ltd., United Kingdom (Aug. 2001).

MacDonald, N. and Burnham, R., "The Effects of Undetected and Untreated Sexually Transmitted Diseases: Pelvic Inflammatory Disease and Ectopic Pregnancy in Canada," *Canadian J. Human Sexuality* 6:161-170, The Sex Information & Education Council of Canada (Sieccan), Canada (1997).

Mashchak, C., et al., "Comparison of pharmacodynamic properties of various estrogen formulations," *Am. J. Obstet. Gynecol.* 144:511-518, Elsevier, United States (1982).

"Medical Management of Endometriosis," Practice Bulletin, No. 11, pp. 1-14, American College of Obstericians and Gynecologists, United States (ACOG) (1999).

Merck Index, 11th ed., Monograph 4112 (Best Available Copy).

Mishell, D., Jr., "Oral Contraception: Past, Present, and Future Perspectives," *Int. J. Fertil.* 36:7-18, MSP International, United States (1991).

Mortola, J., et al., "Diagnosis of Premenstrual Syndrome by a Simple, Prospective, and Reliable Instrument: The Calendar of Premenstrual Experiences," *Obstet. Gynecol.* 76:302-307, Elsevier Science Publishing Co., Inc., United States (1990).

Nelson, A., et al., "Real-World Patterns of Prescription Refills for Branded Hormonal Contraceptives: A Reflection of Contraceptive Discontinuation," *Obstet. Gynecol.* 112:782-787, Lippincott Williams & Wilkins, United States (2008).

Omtzigt, A. and Boerrigter, P., "The effect of 30 ug ethinylestradiol/ 75 ug gestodene and 20 ug ethinylestradiol/150 ug desogestrel on cycle control during normal and extended oral contraceptive intake," *Eur. J. Contracept. Reprod. Health Care* 1:155, Abstract No. FC70, Parthenon Publishing, United Kingdom (1996).

"Oral contraception and depression," *Br. Med. J.* 4:380-381, British Medical Association, United Kingdom (1969).

Philibert, D., et al., "The Pharmacological profile of a novel norpregnane progestin (trimegestone)," Gynecol. Endocrinol. 13:316-326, Parthenon Publishing, United Kingdom (1999).

Phillips, A., et al., "A Comparison of the Potencies and Activities of Progestogens Used in Contraceptives," *Contraception* 36:181-192, Elsevier, United States (1987).

Piper, J. and Kennedy, D., "Oral Contraceptives in the United States: Trends in Content and Potency," *Intl. J. Epidemiology* 16:215-221, Oxford University Press United Kingdom, (1987).

Poindexter, A. et al., "Efficacy and Safety of a 28-day oral contraceptive with 7 days of low-dose estrogen in place of placebo," *Contraception* 78: 113-119, Elsevier, United States (2008).

Portman, D., "Long-Term Safety of an Extended Regimen Oral Contraceptive (Seasonale Lo): A 2-Year Open-Label Trial," [Poster] American Congress of Obstetricians and Gynecologists (ACOG), United States (2006).

Portman, D., "Long-Term Safety of an Extended-Regimen Oral Contraceptive (Seasonale Lo)," *Obstet and Gynecol.* 88S, Lippincott Williams & Wilkins, United States (2006).

Portman, D., et al., "Clinical Trial to Evaluate the Safety and Efficacy of an Extended-Regimen Oral Contraceptive Using Continuous Low-Dose Ethinyl Estradiol," Abstract 4, Contraception 72:229-245, Elsevier, United States (2005).

Reape, K., "Endometrial Effects of an Extended-Regimen Oral Contraceptive With Continuous Low-Dose Estrogen," *Monday Posters 109*:13S (2007).

Reape, K., "Evaluation of the Effects on Serum Hormone Levels of Supplementation with 10 Micrograms Ethyinyl Estradiol Daily During the Typical Hormone-Free Interval of a Combined Oral Contraceptive," *Fert. & Steril. 86*: S15, American Society for Reproductive Medicine Annual Meeting (2006).

Reape, K., "Steady-State Pharmacokinetics of an Extended-Regimen Oral Contraceptive with Continuous Estrogen," [Poster] for DuraMed Research, Inc., United States (2007).

Reape, K., et al., "Effects on serum hormone levels of low-dose estrogen in place of placebo during the hormone-free interval of an oral contraceptive," *Contraception 77*:34-39, Elsevier, United States (2008).

Report of a WHO Scientific Group, "8. Risks with Particular Reference to Neoplasia of Therapeutic Estrogens and Progestins Given to Peri- and Postmenopausal Women," in *Research on the Menopause, World Health Organization*, pp. 52-69, Geneva, Switzerland (1981).

Report of Bleeding observed with Seasonale products as compared to conventional OC products, addendum to Anderson, F.D. and Hait, H., "A multicenter, randomized study of an extended cycle oral contraceptive," *Contraception 68*:89-96, Elsevier, United States (Aug. 2003).

Rittmaster, R., "Hirsutism," Lancet 349:191-195, Lancet Publishing Group, United Kingdom (1997).

Romano, S., et al., "The Role of Fluoxetine in the Treatment of Premenstrual Dysphoric Disorder," *Clin. Ther. 21*:615-633, Excerpta Medica, Inc., United States (1999).

Rosenberg, M. and Waugh, M., "Oral contraceptive discontinuation: A prospective evaluation of frequency and reasons," *Am. J. Obstet. Gynecol. 179*:577-582, Mosby, Inc., United States (1998).

Rumore, M. and Rumore, J., "Clinical Therapeutics of Endometriosis, Part 2," *Am. Pharm. NS29*:40-44, American Pharmaceutical Association, United States (1989).

Rutter, W., et al., "Women's attitudes to withdrawal bleeding and their knowledge and beliefs about the oral contraceptive pill," *Med. J. Australia 149*:417-419, Australasian Medical Publishing Co., Australia (1988).

Saia, K., "Contraception/Family Planning: Method of Induction Abortion With an Unexpectedly Low Rate of Instrumented Placental Removal," *Obstetrics and Gynecology*:86S, Elsevier Science Publishing Co., Inc., United States (2006).

Schlaff, W., et al., "Manipulation of the pill-free interval in oral contraceptive pill users: the effect on follicular suppression," *Am. J. Obstet. Gynecol. 190*: 943-951, Elsevier, United States (2004).

Schneider, H., et al., eds., "Empfängia-verhütung," Urban & Schwarenberg, Munich, Germany, pp. 7-8 (1996).

SEA-301, Summary Statistics: Observed Total Number of Days of Unscheduled Bleeding and/or Spotting by Cycle: All Treated Patients (Best Available Copy) (May 2004).

"Seasonale," Medical Letter on Drugs and Therapeutics, vol. 46, pp. 9, The Medical Letter, Inc., New Rochelle, NY (Feb. 2004).

Shearman, R., "Oral contraceptive agents," *Med. J. Australia 144*:201-205, Australasian Medical Publishing, Austrailia (1986).

Sheth, A., et al., "A Randomized, Double-Blind Study of Two Combined and Two Progestogen-Only Oral Contraceptives," *Contraception 25*:243-252, Geron-X, Inc., United States (1982).

Silberstein, S. and Merriam, G., "Physiology of the menstrual cycle," *Cephalalgia 20*:148-154, Blackwell Science Ltd., United Kingdom (Apr. 2000).

Speroff, L., et al., eds., "Chapter 2. Oral Contraception," in *A Clinical Guide for Contraception*, pp. 25-117, Lippincott, Williams & Wilkins, United Kingdom (2000).

Stearns, S., "PMS and PMDD in the Domain of Mental Health Nursing," *J. Psychosoc. Nurs. Ment. Health Serv. 39*:16-27, Slack Incorporated, United States (2001).

Steiner, M. and Born, L., "Diagnosis and treatment of premenstrual dysphoric disorder: an update," *Int. Clin. Psychopharmacol. 15(Suppl. 3)*:S5-S17, Lippincott, Williams & Wilkins, United (2000).

Steiner, M., "Premenstrual Syndromes," *Annu. Rev. Med. 48*:447-455, Annual Reviews Inc., United States (1997).

Steiner, M., et al., "Fluoxetine in the Treatment of Premenstrual Dysphoria," *N. Engl. J. Med. 332*:1529-1534, Massachusetts Medical Society, United States (1995).

Sulak, P., "Should your patient be on extended-use OCs?" *Contemp. Ob. Gyn. 48*:35-46, Thomson Healthcare Communications, Canada (Sep. 2003).

Sulak, P., et al., "Acceptance of altering the standard 21-day/7-day oral contraceptive regimen to delay menses and reduce hormone withdrawal symptoms," *Am. J. Obstet. Gynecol. 186*:1142-1149, Mosby, Inc., United States (Jun. 2002).

Sulak, P., et al., "Extending the Duration of Active Oral Contraceptive Pills to Manage Hormone Withdrawal Symptoms," *Obstet. Gynecol. 89*:179-182, Lippincott, Wilkins & Wilkins, United States (1997).

Sulak, P., et al., "Hormone Withdrawal Symptoms in Oral Contraceptive Users," *Obstet. Gynecol. 95*:261-266, Lippincott, Williams & Wilkins, United Kingdom (Feb. 2000).

Szarewski, A. and Guillebaud, J., eds., "Contraception, A User's Handbook," pp. 46, 53, 54, 84, 87, Oxford University Press, Oxford, United Kingdom (1994).

"The 2003 Gallup Study of the Market for Oral Contraceptives," conducted by Multi-Sponsor Surveys, Inc., for Barr Laboratories, Inc., 17 pages (May 2003).

Threlkeld, D., ed., "Oral Contraceptives," in *Drug Facts and Comparisons, Facts and Comparisons*, pp. 257-268, United States (1985).

Vandever, M., et al., "Evaluation of pituitary-ovarian axis suppression with three oral contraceptive regimens," *Contraception 77*: 162-170, Elsevier, United States (2008).

"Vier keer per jaar ongesteld," Intermediair, 2 pages, Intermediair (May 2002).

Vollebregt, J., et al., "A study on Postponement of Menses with Low-Dose Combined Oral Contraceptives—Outcome and Acceptability," *Adv. Contracept. 1*:207, Abstract No. 19, Kluwer Academics, Netherlands (1985).

Walker, A., and Bancroft, J., "Relationship Between Premenstrual Symptoms and Oral Contraceptive Use: A Controlled Study," *Psychosom. Med. 52*:86-96, Lippincott Williams & Wilkins, United States (1990).

Ware, M., et al., "Oral Contraception and Depression," *Br. Med. J. 4*:380-381, British Medical Association, United Kingdom (1969).

Westhoff, C.L., and Anderson, F.D., "Seasonale (30 μg of Ethinyl Estradiol/150 μg of Levonorgestrel) Extended-Regimen Oral Contraceptive: Efficacy and Cycle Control by Body Weight." [Abstract], *Contraception 74*:181-182, (2006).

Weström, L. and Mårdh, P., "Ch. 49. Acute pelvic inflammatory disease (PID)," in *Sexually Transmitted Diseases*, pp. 593-613, 2nd Ed, Holmes, K.K., et al., eds., McGraw-Hill, Inc., New York, NY, United States (1990).

Whitty, C., et al., "The Effect of Oral Contraceptives on Migraine," *Lancet 1*:856-859, Lancet Publishing Company, United Kingdom (1966).

World Health Organization Scientific Group, "8. Risks With Particular Reference To Neoplasia of Therapeutic Estrogens and Progestins Given to Peri- and Postmenopausal Women," in *Research on the Menopause, World Health Organization*, pp. 52-69, Geneva, Switzerland (1981).

Wysocki, S., et al., "Hormonal Contraceptives: Extending the Benefits," *Am. J. Nurse Practitioners 6*:19-29, American College of Nurse Practitioners, United States (Nov./Dec. 2002).

Yonkers, K., "Antidepressants in the Treatment of Premenstrual Dysphoric Disorder," *J. Clin. Psychiatry 58(Suppl. 14)*:4-13, Physicians Post Graduate Press, United States (1997).

Yonkers, K., "Medical Management of Premenstrual Dysphoric Disorder," *J. Gend. Specif. Med. 2*:55-60, Multimedia HealthCare/Freedom United States (1999).

Letter from Andreas Görlich to Barr Laboratories, "Zwei Monatsblutungen pro Jahr sind genug. Gefordert ist die sog. Distanz-Pille," Medical Tribune/Gyne, 1 page (1983).

Letter from Andreas Görlich to Barr Laboratories, "Zwei Monatsblutungen pro Jahr sind genug!" Medical Tribune, Austrian Edition, and Medical Tribune, Swiss Edition, 2 pages (1984).
Letter from Andreas Görlich to Barr Laboratories, "Frauenarzt fordert: Schafft die sinniosen Monatsblutungen ab!" *Cosmopolitan* 9:177, 1 page (1984).
Letter from Andreas Görlich to Barr Laboratories, Inc., entitled "Tablets against pregnancy 'Seasonale'," 2 pages (Jun. 2004).
English language translation of Letter from Andreas Görlich to Barr Laboratories, "Gynecological Sensation or Gray Theory? Menstration only twice a year—how is that possible?," Health Magazine (1984).
English language translation of Letter from Andreas Görlich to Barr Laboratories, "Two "Menstrual Periods" Per Year Are Enough," Medical Tribune/Gyne (1983).
English language translation of Letter from Andreas Görlich to Barr Laboratories, "Gynecologist issues challenge: away with senseless menstrual bleeding!," *Cosmopolitan* 9:177 (1984).
Partial English translation of "Having a period four times per year," Intermediair, 2 pages, Intermediair (May 2002).
Docket Sheet for *Teva Women's Health, Inc.* v. *Lupin, Ltd. et al*, U.S. District Court, District of New Jersey (Newark), most recent entry date of Aug. 1, 2012, 31 pages.
Docket Sheet for *Watson Laboratories, Inc.* v. *Teva Women's Health, Inc.*, U.S. District Court, District of Nevada (Reno) most recent entry date of May 19, 2010, 2 pages.
"Complaint for Declaratory Judgment of Patent Invalidity and Non-Infringement" in *Watson Laboratories, Inc.* v. *Teva Women's Health, Inc.*, U.S. District Court, District of Nevada (Reno), filed Feb. 25, 2010, 29 pages.
Docket Sheet for *Duramed Pharmaceuticals, Inc.* v. *Watson Laboratories, Inc. et al*, U.S. District Court, District of Nevada (Reno), most recent entry date of Jul. 25, 2012, 50 pages.
"Order" in *Duramed Pharmaceuticals, Inc.* v. *Watson Laboratories, Inc. et al*, U.S. District Court, District of Nevada (Reno), filed Mar. 31, 2010, 11 pages.
Docket Sheet for *Teva Women's Health, Inc.* v. *Lupin, Ltd. et al*, U.S. District Court, District of New Jersey (Trenton), most recent entry date of Aug. 3, 2012, 29 pages.
"Answer and Counterclaims of Lupin Pharmaceuticals, Inc. and Lupin, Ltd." in *Teva Women's Health, Inc.* v. *Lupin, Ltd. et al.*, U.S. District Court, District of New Jersey (Trenton), filed Mar. 19, 2010, 16 pages.
Docket Sheet for *Teva Women's Health, Inc.* v. *Mylan Pharmaceuticals, Inc. et al*, U.S. District Court, District of New Jersey (Newark), most recent entry date of Jul. 17, 2012, 17 pages.
Docket Sheet for *Teva Women's Health, Inc.* v. *Mylan Pharmaceuticals, Inc. et al*, U.S. District Court, District of New Jersey (Trenton), most recent entry date of Aug. 3, 2012, 7 pages.
Docket Sheet for *Teva Women's Health, Inc.* v. *Lupin, Ltd., et al*, U.S. District Court, District of New Jersey (Trenton), most recent entry date of Oct. 28, 2011, 4 pages.
Docket Sheet for *Duramed Pharmaceuticals, Inc.* v. *Sandoz Inc.*, U.S. District Court, District of New Jersey (Trenton), most recent entry date of Oct. 15, 2010, 12 pages.
Docket Sheet for *Duramed Pharmaceuticals, Inc.* v. *Watson Laboratories, Inc.*, U.S. Court of Appeals for the Federal Circuit, most recent entry date of May 2, 2011, 4 pages.
"Non-Confidential Brief for Defendant-Appellant" in *Duramed Pharmaceuticals, Inc.* v. *Watson Laboratories, Inc.*, Case No. 10-1331, U.S. Court of Appeals for the Federal Circuit, filed Jun. 28, 2010, 55 pages.
Exhibit 9—Redacted (Part 1 of Expert Report of Patricia J. Sulak, M.D.) to "Redaction to Order on Motion to Seal by Teva Women's Health, Inc." in *Teva Women's Health, Inc.* v. *Lupin, Ltd. et al*, U.S. District Court, District of New Jersey (Newark), filed Aug. 30, 2010, 50 pages.
Exhibit 9—Redacted (Part 2 of Expert Report of Patricia J. Sulak, M.D.) to "Redaction to Order on Motion to Seal by Teva Women's Health, Inc." in *Teva Women's Health, Inc.* v. *Lupin, Ltd. et al*, U.S. District Court, District of New Jersey (Newark), filed Aug. 30, 2010, 48 pages "Exhibit 10—Redacted" (Part 1 of Deposition of Patricia J. Sulak, M.D.) to "Redaction to Order on Motion to Seal by Teva Women's Health, Inc." in *Teva Women's Health, Inc.* v. *Lupin, Ltd. et al*, U.S. District Court, District of New Jersey (Newark), filed Aug. 30, 2010, 101 pages.
"Exhibit 10—Redacted" (Part 2 of Deposition of Patricia J. Sulak, M.D.) to "Redaction to Order on Motion to Seal by Teva Women's Health, Inc." in *Teva Women's Health, Inc.* v. *Lupin, Ltd. et al*, U.S. District Court, District of New Jersey (Newark), filed Aug. 30, 2010, 100 pages.
Exhibit 10—Redacted (Part 3 of Deposition of Patricia J. Sulak, M.D.) to "Redaction to Order on Motion to Seal by Teva Women's Health, Inc." in *Teva Women's Health, Inc.* v. *Lupin, Ltd. et al*, U.S. District Court, District of New Jersey (Newark), filed Aug. 30, 2010, 83 pages.
Notice of Motion for Leave to File First Amended Answer and Counterclaims of Lupin Pharmaceuticals, Inc. and Lupin, Ltd. in *Teva Women's Health, Inc.* v. *Lupin, Ltd. et al*, U.S. District Court, District of New Jersey (Newark), filed Oct. 8, 2010, 27 pages.
"Exhibit B" (Depostion of Howard Hait) to "Motion to Seal by Teva Women's Health, Inc." in *Teva Women's Health, Inc.* v. *Lupin, Ltd. et al*. U.S. District Court, District of New Jersey (Newark), filed Jul. 13, 2010, 92 pages.
"Exhibit D" (Deposition of Kathleen Z. Reape, M.D.) to "Motion to Seal by Teva Women's Health, Inc." in *Teva Women's Health, Inc.* v. *Lupin, Ltd. et al*, U.S. District Court, District of New Jersey (Newark), filed Jul. 13, 2010, 49 pages.
"Defendants Watson Laboratories, Inc. and Watson Pharmaceuticals, Inc.'s Brief in Opposition to Plantiffs Motion to Dismiss/Strike Watson's Inequitable Conduct Counterclaim and Defense" in *Teva Women's Health, Inc.* v. *Lupin, Ltd. et al*, filed Jul. 23, 2010, 44 pages.
"Exhibit 26, Part 1" (Mircette® NDA 20-713) to "Request for Judicial Notice Regarding Reply to Response to Motion by Plaintiff Duramed Pharmaceuticals, Inc." in *Duramed Pharmaceuticals, Inc.* v. *Watson Laboratories, Inc. et al*, U.S. District Court, District of Nevada (Reno), filed Jun. 14, 2011, 40 pages.
"Exhibit 26, Part 2" (Mircette® NDA 20-713) to "Request for Judicial Notice Regarding Reply to Response to Motion by Plaintiff Duramed Pharmaceuticals, Inc." in *Duramed Pharmaceuticals, Inc.* v. *Watson Laboratories, Inc. et al*, U.S. District Court, District of Nevada (Reno), filed Jun. 14, 42 pages.
"Exhibit 26, Part 3" (Mircette® NDA 20-713) to "Request for Judicial Notice Regarding Reply to Response to Motion by Plaintiff Duramed Pharmaceuticals, Inc." in *Duramed Pharmaceuticals, Inc.* v. *Watson Laboratories, Inc. et al*, U.S. District Court, District of Nevada (Reno), filed Jun. 14, 2011, 42 pages.
"Second Declaration of Patricia J Sulak, Af.D. in Support of Duramed's Emergency Motion for a Temporary Restraining Order and Preliminary Injuction" in *Duramed Pharmaceuticals, Inc.* v. *Watson Laboratories, Inc. et al*, U.S. District Court, District of Nevada (Reno), filed Jun. 14, 2011, 6 pages.
Defendant-Appellant Watson Laboratories,Inc.'s Reply Brief in *Duramed Pharmaceuticals, Inc.* v. *Watson Laboratories, Inc.*, U.S. Court of Appeals for the Federal Circuit, filed Sep. 30, 2010, 30 pages.
"Judgment" in *Duramed Pharmaceuticals, Inc.* v. *Watson Laboratories, Inc.*, U.S. Court of Appeals for the Federal Circuit, decided Mar. 25, 2011, 20 pages.
Docket Sheet for *Duramed Pharmaceuticals* v. *Watson Labs*, U.S. Court of Appeals for the Federal Circuit, most recent entry date of Feb. 15, 2012, 5 pages.
"First Amended Answer, Affirmative Defenses and Counterclaims of Defendants Watson Laboratories, Inc. and Watson Pharmaceuticals, Inc. to Teva Women's Health, Inc.'s Complaint" in *Teva Woman's Health, Inc.* v. *Lupin Ltd. et al.*, U.S. District Court, District of New Jersey (Newark), filed May 28, 2010, 45 pages, including Exhibit A.
"Reply of Lupin Pharmaceuticals, Inc. and Lupin, Ltd. in Further Support of Motion for Leave to File First Amended Answer and Counterclaim" in *Teva Women's Health, Inc.* v. *Lupin Ltd. et al*, U.S. District Court, District of New Jersey (Newark), filed Nov. 15, 2010, 15 pages.

"Exhibit to Letter by Lupin Pharmaceuticals, Inc. et al. (Lupin's First Amended Invalidity and Non-Infringement Contentions)" in *Teva Women's Health, Inc.* v. *Lupin, Ltd. et al*, filed Nov. 29, 2010, 25 pages.

"Mylan/Famy Care Exhibit A to Letter by Lupin Pharmaceuticals, Inc. et al. (Defendant's Supplemental Non-Infringement and Invalidity Contentions)" in *Teva Women's Health, Inc.* v. *Mylan Pharmaceuticals, Inc. et al.*, filed Nov. 29, 2010, 146 pages.

"Watson Exhibit 1 to Letter by Lupin Pharmaceuticals, Inc. et al. (Defendants Watson Pharmaceutical's, Inc.'s and Watson Laboratories Inc.'s Supplemental Invalidity and Non-Infringement Contentions)" in *Teva Women's Health, Inc.* v. *Lupin, Ltd. et al.*, filed Nov. 29, 2010, 100 pages.

"First Amended Answer and Counterclaims of Lupin Pharmaceuticals, Inc. and Lupin, Ltd." in *Teva Women's Health, Inc.* v. *Lupin Ltd. et al*, U.S. District Court, District of New Jersey (Newark), filed Dec. 8, 2010, 14 pages.

Approval History for DESOGESTREl; ETHINYL ESTRADIOL (Generic Name), Abreviated New Drug Application 75-256, Food and Drug Administration, 1999, 72 pages, available http://www.accessdata.fda.gov/scripts/cder/drugsatfda/.

Approval History for CYCLESSA, New Drug Application 21-090, Food and Drug Administration, 1999, 76 pages, available at: http://www.accessdata.fda.gov_/scripts/cder/drugsatfda/.

Labeling Revision for DESOGEN, Organon USA Inc., Roseland, NJ Nov. 13, 2006, 69 pages, available at:http://www_.accessdata.fda.gov/scripts/_cder/drugsatfda/ as New Drug Application 20-071, Food and Drug Administration (original approval Dec. 10, 1992).

Tentative Approval Letter and Approval Letter for KARIVA, Abreviated Administration New Drug Application 75-863, Food and Administration, Nov. 29, 2001 and Apr. 5, 2002, 9 pages, available at http://www.accessdata.fda.gov/scrpts/cder/drugsatfda/.

Annex I of Declaration of Dr. Anne Szarewski: Szarewski, A., Curriculum Vitae, 14 pages (Apr. 2004).

Annex II of Declaration of Dr. Anne Szarewksi: "Commercially Available Monophasic Combined Oral Contraceptive Pills," and "Ratio of equivalence given in patent EP 0 911 029 B1" (Apr. 2004).

Annex III of Declaration of Dr. Anne Szarewksi: Belsey, E., "The Association Between Vaginal Bleeding Patterns and Reasons for Discontinuation of Contraceptive Use," *Contraception* 38:207-225, Elsevier, United States (1988).

Annex IV of Declaration of Dr.Anne Szarewksi: Benaglano, G. and Fraser, I., "The Depo-Provera Debate, Commentary on the Article Depo-Provera, A Critcal Analysis," *Contraception* 24:493-528, Elsevier, United States (1981).

Annex V of Declaration of Dr. Anne Szarewski: "Is Cerazette the minipill of choice?" *Drug Ther. Bull.* 41:1-3, Consumers' Association, United Kingdom (Sep. 2003).

Annex VI of Declaration of Dr. Anne Szarewski: Committee for Proprietary Medicinal Products, Note for Guidance on Clinical Investigation of Steroid Contraceptives in Women, 5 pages, The European Agency for the Evaluation of Medicinal Products (Feb. 2000).

Annex VII of Declaration of Dr. Anne Szarewski: Goldzieher, J. and Fortherby, K., eds., "Pharmacology of the Contraceptive Steroids," pp. 82-86, Raven Press, New York, NY, United States (1994).

Annex VIII of Declaration of Dr. Anne Szarewski: Guillebaud, J., ed., "The pill: how do I take it?," in *The Pill and Other Hormones for Contraception*, pp. 52-53, 110-113, 182-183, 190-191, Oxford University Press, Great Britain, United Kingdom (1991).

Annex IX of Declaration of Dr. Anne Szarewski: Adams Hillard, P., "The patient's reaction to side effects of oral contraceptives," *Am. J. Obstet. Gynecol.* 161:1412-1415, Mosby-Year Book, United States (1989).

Annex X of Declaration of Dr. Anne Szarewski: International Working Group, "A consensus statement: enhancing patient compliance and oral contraceptive efficacy," *Brit. J. Fam. Planning* 18:126-129, Faculty of Family Planning and Reproductive Health Care, United Kingdom (1993).

Annex XI of Declaration of Dr. Anne Szarewski: Korver, T., for the Collaborative Study Group, "A double-blind study comparing the contraceptive efficacy, acceptability and safety of two progestogen-only pills containing desogestrel 75 µg/day or levonorgestrel 30 µg/day," *Eur. J. Contra. Reprod. Health Care* 3:169-178, Parthenon Publishing (1998).

Annex XII of Declaration of Dr. Anne Szarewski: Larsson, K. and Machin, D., "Predictability of the safety of hormonal contraceptives from canine toxicological studies, " in *Safety requirements for contraceptive steroids*, Michael D., ed., Cambridge University Press, Oxford, United Kingdom (1989).

Annex XIII of Declaration of Dr. Anne Szarewski: Lumbiganon, P., "Depot-medroxyprogesterone acetate (DMPA) and cancer of the endometrium and ovary," *Contraception* 49:203-209, Butterworth Heinemann, United States (1994).

Annex XIV of Declaration of Dr. Anne Szarewski: Rice, C., et al., "A comparison of the inhibition of ovulation achieved by desogestrel 75 µg and levnorgestrel 30 µg daily," *Human Reprod.* 14:982-985, Oxford University Press, United Kingdom (1999).

Annex XV of Declaration of Dr. Anne Szarewski: Rosenberg, M. and Waugh, M., "Causes and consequences of oral contraceptive noncompliance," *Am. J. Obstet. Gnyecol.* 180:S276-S279, Mosby, Inc., United States (1999).

Annex XVI of Declaration of Dr. Anne Szarewski: Rosenberg, M., et al., "Use and Misuse of Oral Contraceptives: Risk Indicators for Poor Pill Taking and Discontinuation," *Contraception* 51:283-288, Elsevier Science Inc., United States (1995).

Annex XVII of Declaration of Dr. Anne Szarewski: Rosenfield, A., et al., "The Food and Drug Administration and Medroxyprogesterone Acetate," *JAMA* 249:2922-2928, American Medical Association, United States (1983).

Annex XVIII of Declaration of Dr. Anne Szarewski: Szarewski, A., ed., "Figure 3.5 Oestrogen-dominant and progestogen-dominant pills," in *Hormonal Contraception: A Women's Guide*, pp. 45, Macdonald Optima, United Kingdom (1991).

Annex XIX of Declaration of Dr. Anne Szarewski: Szarewski, A. and Guillebaud, J., eds., "Which Pill will Suit me Best?," in *Contraception, A User's Handbook*, pp. 43-72, Oxford University Press, United Kingdom (1994).

Annex XX of Declaration of Dr. Anne Szarewski: Wilkinson, C. and Szarewski, A., eds., "Management of Breakthrough Bleeding," in *Contraceptive Dilemmas*, Altman Publishing, pp. 4-7, St. Albans, Englan (2003).

Annex XXI of Declaration of Dr. Anne Szarewski: WHO Collaborative Study Group, "Depot-Medroxyprogesterone Acetate (DMPA) and Risk of Endometrial Cancer," *Int. J. Cancer* 49:186-190, Wiley-Liss, Inc., United States (1991).

Annex XXII of Declaration of Dr. Anne Szarewski: WHO Collaborative Study Group, "Breast cancer and depot-medroxyprogesterone acetate: a multinational study," *Lancet* 338:833-838, Lancet Publishing Company, United Kingdom (1991).

Notice and Statement of Opposition filed by Schering AG in Opposition to EP 0 911 029 B1, 33 pages (Jan. 2003).

Facts About Seasonale®, Barr Laboratories, Inc., 1 page (published after Sep. 5, 2003).

Seasonale®, Product Description and Information, Duramed Pharmaceuticals, Inc., 39 pages (Revised Sep. 2003).

Decision revoking the European Patent No. EP 0 911 029 B issued by European Patent Office (Jul. 2004).

Further Submission "Urgent—Oral Proceedings on Jun. 8, 2004," European Patent Office, Germany, 2 pages (May 2004).

Further Submission "Urgent—Oral Proceedings Scheduled for Aug. 6, 2004," European Patent Office, Germany, 2 pages (May 2004).

Response to Communication of Notices of Opposition for European Patent No. 0 911 029 in EPO, European Patent Office, Germany, 9 pages (Oct. 2003).

Summons to Attend Oral Proceedings Pursuant to Rule 71(1) EPC, issued by European Patent Office, Germany, 1 page (Jan. 2004).

Written Submission, with new Main and Auxiliary Requests, European Patent Office, Germany 22 pages (Apr. 2004).

Declaration by Alan H. DeCherney, M.D., with Curriculum Vitae, Alan Hersh DeCherney, M.D., 60 pages (Nov. 2004).

International Search Report for International Appl. No. PCT/US02/38602, filed on Jul. 19, 2004, European Patent Office, Munich, Germany.

International Search Report for International Appl. No. PCT/US04/ 11543, filed on Apr. 14, 2004, ISA/US, Alexandria, VA, mailed on Feb. 25, 2005.

International Search Report for International Application No. PCT/US04/13589, ISA/US, Alexandria, VA, mailed on Mar. 9, 2006.

Written Opinion for International Application No. PCT/US04/ 013589, completed on Nov. 11, 2005, Alexandria, Virginia.

Written Opinion for International Application No. PCT/US04/ 22829, completed on Sep. 18, 2006, U.S. Patent Office, Alexandria, Virginia.

International Search Report for International Application No. PCT/US04/22829, United States Patent and Trademark Office, United States, mailed on Oct. 16, 2006.

Supplemental European Search Report for EP Patent Appl. No. 04760680, European Patent Office, Munich, Germany, mailed Jan. 22, 2009.

Supplemental Partial European Search Report for European Patent Application No. EP 04 77 8369, dated Aug. 19, 2009, The Hague, The Netherlands.

Miller, L. and Hughes, J.P., "Continuous Combination Oral Contraceptive Pills to Eliminate Withdrawal Bleeding: A Randomized Trial," *Obstetrics & Gynecology 101*: 653-681, Elsevier (Apr. 2003).

Rosenberg, M.J. et al., "Efficacy, Cycle Control, and side Effects of Low- and Lower-Dose Oral Contraceptives: A Randomized Trial of 20 μg and 35 μg Estrogen Preparations," *Contraception 60*:321-329, Elsevier (2000).

Rowan, J.P., "'Estrophasic' dosing: A new concept in oral contraceptive therapy," *Am. J. Obstet. Gynecol. 180*:S302-S306, Mosby, Inc. (1999).

Sucato, G.S., et al., "Extended Cycling of Oral Contraceptive Pills for Adolescents," *J. Pediatr. Adolesc. Gynecol. 15*:325-327, Elsevier (2002).

Declaration of Dr. Anne Szarewski from Opposition to EP 0 911 029 B1 by Schering AG, 8 pages (Apr. 2004).

Appellant's Grounds of Appeal, with Main Request and First, Second, Third, Fourth, Fifth and Sixth Auxiliary Requests in Opposition in EP 0 911 029 B1; 37 pages (Nov. 2004).

Notice of Opposition by Akzo Nobel N.V. in EP 0 911 029 B1, 8 pages (Jan. 2002).

"Defendant Watson Laboratories, Inc.'s Opposition to Plaintiff's Motion for TRO/Preliminary Injunction" in *Duramed Pharmaceuticals, Inc. v. Watson Laboratories, Inc., et al.*, U.S. District Court, District of Nevada (Reno), filed Jun. 13, 2011, 32 pages.

Co-Pending U.S. Appl. No. 13/600,050, filed Aug. 30, 2012; Not Yet Published.

Küpper, C., and Loch, E.-G., "Prämenstruelles Syndrom," *Deutsche Apotheker Zeitung 136*:23-29,:23-29, Deutcher Apotheker Verlag (1996).

Schneider, H., et al., eds., "Empfängnis-verhütung," Urban & Schwarzenberg, Munich, Germany, pp. 7-8 (1996).

"*Defendant Watson Laboratories, Inc.'s Opposition to Plaintiff's Motion for TRO/Preliminary Injunction*" in *Duramed Pharmaceuticals, Inc. v.Watson Laboratories, Inc. et al*, U.S. District Court, District of Nevada (Reno), filed Jun. 13, 2011, 32 pages.

Drugs@FDA: FDA Approved Drug Products. "Seasonique," accessed on Oct. 23, 2012, accessed at the World Wide Web at accessdata.fda.gov/Scripts/cder/DrugsatFDA/index.cfm?fuseaction=Search.DrugDetails.

\* cited by examiner

METHODS OF HORMONAL TREATMENT UTILIZING ASCENDING-DOSE EXTENDED CYCLE REGIMENS

CROSS REFERENCE TO RELATED APPLICATIONS

This application is a divisional of U.S. application Ser. No. 11/892,026, filed Aug. 17, 2007, which is a continuation of U.S. application Ser. No. 11/554,571, filed Oct. 30, 2006, which is a continuation in part of U.S. application Ser. No. 11/245,471, filed Oct. 7, 2005, which claims the benefit of U.S. Provisional Application No. 60/616,424, filed Oct. 7, 2004, and U.S. Provisional Application No. 60/684,568, filed May 26, 2005, the contents of which are hereby incorporated by reference in their entireties.

BACKGROUND OF THE INVENTION

1. Field of the Invention

The present invention relates to methods of hormonal treatment by ascending-dose extended administration of an estrogen and a progestin.

2. Related Art

The human menstrual cycle involves a repetitive sequence of hormonal changes that result in episodic uterine bleeding. Normally, each menstrual cycle has a mean interval of 21 to 35 days, conventionally beginning with the first day of menstrual flow and ending on the day before the next onset of bleeding. Duration of the menstrual now is usually 2 to 6 days with loss of about 20 to about 60 ml of blood.

The menstrual cycle is divided into follicular and luteal phases, each corresponding to changes occurring in the ovary. These phases may also be described as proliferative or secretory, corresponding to changes observed in the uterine endometrium. Variations in the length of the cycle are usually due to alterations in the follicular phase, because the luteal phase length remains relatively constant at 12 to 16 days.

During the follicular phase, several primary follicles are recruited for further growth and development. Granulosa cells in primary follicles possess follicle stimulating hormone (FSH) and estradiol receptors. Upon FSH stimulation, granulosa cells produce aromatase. This enzyme converts the androgens androstenedione and testosterone, made in response to luteinizing hormone (LH) by thecal cells, to estrone and estradiol, respectively. Granulosa cells respond to estradiol by undergoing mitosis to increase the number of granulosa cells and estradiol production. By day 7 of the cycle, one enlarging primary follicle is selected by unknown processes to be the follicle that will release the oocyte at ovulation.

The midcycle rise in plasma estradiol stimulates the large midcycle LH surge. This midcycle LH surge triggers resumption of meiosis within the oocyte and luteinization of the granulosa cells within the preovulatory follicle. Immediately before ovulation, the outer follicular wall begins to dissolve and an oocyte is released approximately 24 to 36 hours from the onset of the LH surge.

After ovulation, granulosa cells and the surrounding theca cells enlarge, accumulate lipid, and become transformed into lutein cells. This begins the luteal phase of the menstrual cycle. These cells form a new vascularized structure called the corpus luteum, which secretes estradiol and progesterone. LH maintains the corpus luteum during the luteal phase and, acting via the adenyl cyclase system, stimulates progesterone production. If pregnancy does not occur, lutein cells degenerate, and diminished hormone secretion precedes menstruation. Menstruation is immediately followed by the onset of another menstrual cycle.

Because endometrial proliferation serves to prepare the uterus for an impending pregnancy, manipulation of hormones and of the uterine environment can provide contraception. For example, estrogens are known to decrease FSH secretion by feedback inhibition. Under certain circumstances, estrogens can also inhibit LH secretion, once again by negative feedback. Under normal circumstances, the spike of circulating estrogen found just prior to ovulation induces the surge of gonadotropic hormones that occurs just prior to and results in ovulation. High doses of estrogen immediately post-coitally also can prevent conception probably due to interference with implantation.

Progestins can also provide contraception. Endogenous progesterone after estrogen is responsible for the progestational changes of the endometrium and the cyclic changes of cells and tissue in the cervix and the vagina. Administration of progestin makes the cervical mucus thick, tenacious and cellular which is believed to impede spermatozoal transport. Administration of progestin also inhibits luteinizing hormone secretion and blocks ovulation in humans.

The most prevalent form of oral contraception is a pill that combines both an estrogen and a progestin, a so-called combined oral contraceptive preparation. Alternatively, there are contraceptive preparations that comprise progestin only. However, the progestin-only preparations have a more varied spectrum of side effects than do the combined preparations, especially more breakthrough bleeding. As a result, the combined preparations are the preferred oral contraceptives in use today (Sheth et. al., *Contraception* 25:243 (1982)).

Whereas the conventional 21 day pill packs with a 7 day placebo interval worked well when oral contraceptives were of higher dosage, as the doses have come down, for both the estrogen and progestin components, bleeding problems have increased in frequency, especially in the early months of oral contraceptive use, but even persistently so in some patients.

There exists a need for contraceptives that reduce bleeding problems and/or have additional benefits for women.

BRIEF SUMMARY OF THE INVENTION

The present invention provides ascending-dose extended cycle regimens in which a female is administered an estrogen and a progestin for a period of greater than 30 or 31 consecutive days, optionally followed by a hormone-free period of 2 to 10 consecutive days or by administration of estrogen for a period of 2 to 10 consecutive days.

The present invention is directed to a method of contraception, the method comprising administering to a female in need thereof an estrogen and a progestin for a period of greater than 30 or 31 consecutive days, wherein the estrogen and progestin are administered in at least three phases, wherein a daily dosage of estrogen in a second phase is equal to or higher than a daily dosage of estrogen in a first phase, wherein a daily dosage of estrogen in a third phase is equal to or higher than the daily dosage of estrogen in the second phase, wherein a total daily dosage of estrogen and progestin in the second phase is higher than a total daily dosage of estrogen and progestin in the first phase, and wherein a total daily dosage of estrogen and progestin in the third phase is higher than the total daily dosage of estrogen and progestin in the second phase.

The present invention is also directed to a method of contraception, the method comprising administering to a female in need thereof an estrogen and a progestin for a period of greater than 30, 31, or 42 consecutive days, wherein the estrogen and progestin are administered in at least two phases, wherein a total daily dosage of estrogen and progestin in a second phase is higher than a total daily dosage of estrogen and progestin in a first phase, and wherein a daily dosage of progestin in the second phase is less than twice a daily dosage of progestin in the first phase.

The ascending-dose extended cycle regimens provide a number of non-contraceptive benefits, as well as contraceptive benefits. For example, the present invention is also directed to a method of reducing breakthrough bleeding in a female in need thereof by administering to the female an ascending-dose extended cycle regimen disclosed herein.

DETAILED DESCRIPTION OF THE INVENTION

The present invention is directed to ascending-dose extended cycle regimens that are useful in the treatment of a variety of conditions and disorders occurring in females of child-bearing age, in peri-menopausal females, and/or in menopausal females. In accordance with the present invention, a female is administered an ascending-dose extended cycle regimen of an estrogen and a progestin (or progestogen) for a period of greater than 30 or 31 consecutive days.

An "ascending-dose extended cycle regimen" of the present invention refers to a regimen disclosed herein in which an estrogen and a progestin are administered for a period of greater than 30 or 31 consecutive days, wherein the estrogen and progestin are administered in at least three phases, wherein a daily dosage of estrogen in a second phase is equal to or higher than a daily dosage of estrogen in a first phase, wherein a daily dosage of estrogen in a third phase is equal to or higher than the daily dosage of estrogen in the second phase, wherein a total daily dosage of estrogen and progestin in the second phase is higher than a total daily dosage of estrogen and progestin in the first phase, and wherein a total daily dosage of estrogen and progestin in the third phase is higher than the total daily dosage of estrogen and progestin in the second phase.

An "ascending-dose extended cycle regimen" of the present invention also refers to a regimen disclosed herein in which an estrogen and a progestin are administered for a period of greater than 30, 31, or 42 consecutive days, wherein the estrogen and progestin are administered in at least two phases, wherein a total daily dosage of estrogen and progestin in a second phase is higher than a total daily dosage of estrogen and progestin in a first phase, and wherein a daily dosage of progestin in the second phase is less than twice a daily dosage of progestin in the first phase.

As used herein, "extended cycle regimen" refers to a regimen in which a contraceptive composition is administered for a period of greater than 30 or 31 days.

As used herein, "female" refers to any animal classified as a mammal, including humans and non-humans, such as, but not limited to, domestic and farm animals, zoo animals, sports animals, and pets.

"Peri-menopausal female" refers to a woman who has not yet definitely arrived at menopause but who is experiencing symptoms associated with menopause. "Peri-menopause" means "about or around the time of menopause." It encompasses the years preceding the last menstrual period during which ovarian function declines and ultimately ceases and can include the presence of symptoms and irregular cycles. "Menopausal female" refers to a woman who has definitely arrived at menopause and may be experiencing symptoms associated with menopause. Menopause or post-menopause is the permanent cessation of menstruation after the loss of ovarian activity and is generally defined clinically as the absence of menstruation for about one year. Menopause may occur naturally in a woman or it may be artificially induced, e.g., through surgical or chemical means. For example, removal of the ovaries, which can occur, e.g., through hysterectomy, frequently leads to symptoms associated with menopause.

The terms "treat" and "treatment" refer to both therapeutic treatment and prophylactic or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment.

The term "continuous" or "consecutive" in reference to "administration" means that the frequency of administration is at least once daily. Note, however, that the frequency of administration can be greater than once daily and still be "continuous," e.g., twice or even three times daily, as long as the dosage levels as specified herein are not exceeded.

The term "daily dosage," "daily dosage level," "daily dosage amount," or "daily dose" means the total amount of estrogen (and/or progestin) administered per day. Thus, for example, "continuous administration" of a progestin to a woman at a "daily dosage level" of 30 μg means that the woman receives a total of 30 μg of progestin on a daily basis, whether the progestin is administered as a single 30 μg dose or, e.g., three separate 10 μg doses. A conventional means of continuously administering an estrogen or progestin is as a single daily oral dose at the prescribed daily dosage level.

As used herein, "about" refers to plus or minus 10% of the indicated number. For example, "about 10 μg" indicates a range of 9 μg to 11 μg.

Dosages and Regimens

The present invention is directed to a method of providing an ascending-dose extended cycle regimen, the method comprising administering to a female in need thereof an estrogen and a progestin for a period of greater than 30 or 31 consecutive days, wherein the estrogen and progestin are administered in at least three phases, wherein a daily dosage of estrogen in a second phase is equal to or higher than a daily dosage of estrogen in a first phase, wherein a daily dosage of estrogen in a third phase is equal to or higher than the daily dosage of estrogen in the second phase, wherein a total daily dosage of estrogen and progestin in the second phase is higher than a total daily dosage of estrogen and progestin in the first phase, and wherein a total daily dosage of estrogen and progestin in the third phase is higher than the total daily dosage of estrogen and progestin in the second phase.

The present invention is also directed to a method of providing an ascending-dose extended cycle regimen, the method comprising administering to a female in need thereof an estrogen and a progestin for a period of greater than 30, 31, or 42 consecutive days, wherein the estrogen and progestin are administered in at least two phases, wherein a total daily dosage of estrogen and progestin in a second phase is higher than a total daily dosage of estrogen and progestin in a first phase, and wherein a daily dosage of progestin in the second phase is less than twice a daily dosage of progestin in the first phase.

In some aspects of the invention, the daily dosage of progestin in the first and second phases are equal to each other. In further aspects of the invention, the daily dosages of progestin in the first, second, and third phases are equal to each other. The daily dosage of progestin can be, but is not limited to, the equivalent of 150 μg of levonorgestrel for the first, second, and third phases.

In some aspects of the invention, the daily dosage of progestin in the second phase is higher than the daily dosage of progestin in the first phase. In further aspects of the invention, the daily dosage of progestin in the third phase is higher than the daily dosage of progestin in the second phase.

In some aspects of the invention, the daily dosage of progestin in the second phase is equal to the daily dosage of progestin in the first phase and the daily dosage of progestin in the third phase is higher than the daily dosage of progestin in the second phase. In other aspects of the invention, the daily dosage of progestin in the second phase is higher than the daily dosage of progestin in the first phase and the daily dosage of progestin in the third phase is equal to the daily dosage of progestin in the second phase.

In some aspects of the invention, the daily dosage of progestin in the second phase is less than twice the daily dosage of progestin in the first phase. In further aspects of the invention, the daily dosage of progestin in the third phase is less than twice the daily dosage of progestin in the second phase.

The daily dosage of progestin in the first phase can be, but is not limited to, the equivalent of 95 μg to 105 μg, 97 μg to 102 μg, or 99 μg to 101 μg of levonorgestrel. For example, the daily dosage of progestin in the first phase can be the equivalent of 100 μg levonorgestrel. The daily dosage of progestin in the second phase can be, but is not limited to, the equivalent of 120 μg to 130 μg, 122 μg to 128 μg, or 124 μg to 126 μg of levonorgestrel. For example, the daily dosage of progestin in the second phase can be the equivalent of 125 μg of levonorgestrel. The daily dosage of progestin in the third phase can be, but is not limited to, the equivalent of 145 μg to 155 μg, 147 μg to 153 μg, or 149 μg to 151 μg of levonorgestrel. For example, the daily dosage of progestin in the third phase can be the equivalent of 150 μg of levonorgestrel.

In some aspects of the invention, the progestin used is trimegestone. The total daily dosage of trimegestone can be, but is not limited to, 0.25 mg to 2.0 mg, 0.5 mg to 1.5 mg, 0.75 mg to 1.25 mg, or 1.0 mg. In those aspects of the invention in which trimegestone is administered transdermally or vaginally, the total daily dosage of trimegestone can be, but is not limited to, 0.175 mg to 2.0 mg, 0.35 mg to 1.5 mg, 0.52 mg to 1.25 mg, or 0.7 mg to 1.0 mg.

In further aspects of the invention, the daily dosage of trimegestone in the first and second phases of an ascending-dose extended cycle regimen can be 1.0 mg. In still further embodiments, the daily dosage of trimegestone in the first, second, and third phases of an ascending-dose extended cycle regimen can be 1.0 mg. In those aspects of the invention in which trimegestone is administered transdermally or vaginally, the daily dosage of trimegestone in the first and second phases of an ascending-dose extended cycle regimen can be 0.7 mg to 1.0 mg. In yet other embodiments, the daily dosage of transdermally- or vaginally-administered trimegestone in the first, second, and third phases of an ascending-dose extended cycle regimen can be 0.7 mg to 1.0 mg.

The daily dosage of trimegestone in the first phase can be, but is not limited to, 0.25 mg to 1.25 mg, 0.5 mg to 1.0 mg, or 0.75 mg. The daily dosage of trimegestone in the second phase can be, but is not limited to, 0.5 mg to 1.5 mg, 0.75 mg to 1.25 mg, or 1.0 mg. The daily dosage of trimegestone in the third phase can be, but is not limited to, 0.75 mg to 1.75 mg, 1.0 mg to 1.5 mg, or 1.25 mg.

For those aspects of the invention in which the trimegestone is administered transdermally or vaginally, the daily dosage of trimegestone in the first phase can be, but is not limited to, 0.175 mg to 1.25 mg, 0.35 mg to 1.0 mg, or 0.52 mg to 0.75 mg. The daily dosage of transdermally- or vaginally-administered trimegestone in the second phase can be, but is not limited to, 0.35 mg to 1.5 mg, 0.52 mg to 1.25 mg, or 0.7 mg to 1.0 mg, and the daily dosage in the third phase can be, but is not limited to, 0.52 mg to 1.75 mg, 0.7 mg to 1.5 mg, or 0.87 mg to 1.25 mg.

The trimegestone can be administered together with an estrogen in the ascending-dose extended cycle regimens of the present invention. In addition, the trimegestone can be administered in combination with an estrogen in other oral contraceptive regimens.

For example, the daily dosage of trimegestone for an estrogen and progestin combined 28-day oral contraceptive can be, but is not limited to, 0.25 mg to 2.0 mg, 0.5 mg to 1.75 mg, 0.75 mg to 1.25 mg, or 1.0 mg.

In some aspects of the invention, the daily dosage of estrogen in each of the first and second phases are equal to each other. In further aspects of the invention, the daily dosage of estrogen in each of the first, second, and third phases are equal to each other.

In some aspects of the invention, the daily dosage of estrogen in the second phase is higher than the daily dosage of estrogen in the first phase. In further aspects of the invention, the daily dosage of estrogen in the third phase is higher than the daily dosage of estrogen in the second phase.

In some aspects of the invention, the daily dosage of estrogen in the second phase is equal to the daily dosage of estrogen in the first phase and the daily dosage of estrogen in the third phase is higher than the daily dosage of estrogen in the second phase. In other aspects of the invention, the daily dosage of estrogen in the second phase is higher than the daily dosage of estrogen in the first phase and the daily dosage of estrogen in the third phase is equal to the daily dosage of estrogen in the second phase.

In some aspects of the invention, the daily dosage of estrogen in the second phase is less than twice the daily dosage of estrogen in the first phase. In further aspects of the invention, the daily dosage of estrogen in the third phase is less than twice the daily dosage of estrogen in the second phase.

In some aspects of the invention, the daily dosage of estrogen in the first phase is the equivalent of 15 μg to 25 μg, 17 μg to 23 μg, or 19 μg to 21 μg of ethinyl estradiol. For example, the daily dosage of estrogen in the first phase can be the equivalent of 20 μg of ethinyl estradiol.

In some aspects of the invention, the daily dosage of estrogen in the second phase is the equivalent of 20 μg to 30 μg, 22 μg to 28 μg, or 24 μg to 26 μg of ethinyl estradiol. For example, the daily dosage of estrogen in the second phase can be the equivalent of 25 μg of ethinyl estradiol.

In some aspects of the invention, the daily dosage of estrogen in the third phase is the equivalent of 25 μg to 35 μg, 27 μg to 33 μg, or 29 μg to 31 μg of ethinyl estradiol. For example, the daily dosage of estrogen in the third phase can be the equivalent of 30 μg of ethinyl estradiol.

In some aspects of the invention, the estrogen and progestin are administered orally and the daily dosage of estrogen is the equivalent of 15 µg to 50 µg of ethinyl estradiol and the daily dosage of progestin is the equivalent of 100 µg to 150 µg of levonorgestrel.

In some aspects of the invention, the estrogen and progestin of the ascending-dose extended cycle regimens can be ethinyl estradiol and levonorgestrel, although other suitable estrogens and progestins can be employed. If a different estrogen or progestin is employed, an adjustment in the amount based on the relative potency or activity can be made. Correlations in potency among the various estrogens and among the various progestins are known. See, for example, EP 0 253 607, which is incorporated herein in its entirety by reference. For example, 30 µg of ethinyl estradiol is about the equivalent of 60 µg of mestranol or 2,000 µg of 17β-estradiol. Similarly, 0.050 mg of levonorgestrel is about the equivalent of 0.175 mg of norethindrone acetate, 0.050 mg of desogestrel, 0.050 mg 3-ketodesogestrel, 0.035 mg of gestodene, 0.100 mg of norgestrel, or 0.35-0.50 mg of trimegestone. It should be understood that when norgestrel is used in place of levonorgestrel, its concentration is twice that of levonorgestrel. Norgestrel (dl-norgestrel) is a racemic mixture of optically active isomers, while levonorgestrel is one of the optically active isomers present in norgestrel.

Equivalent concentrations of estrogens and of progestins can be determined using either in vitro or in vivo assay methods. See, for example, Kuhl, H., *Drugs* 51(2):188-215 (1996); Philibert, D., et al., *Gynecol. Endocrinol.* 13:316-326 (1999); and Lundeen, S., et al., *J. Steroid Biochem. Molec. Biol.* 78:137-143 (2001), in which the relative potencies of various progestins are compared using both in vitro and in vivo test assays. See also, for example, Dickey, R. P., "Contraceptive Therapy," *OBG Management Supplement* (October 2000), pp. 2-6. Each of these documents is incorporated herein by reference in its entirety.

For example, various combinations of progestin and estrogen that have been used in oral contraceptives are shown in Table 1.

TABLE 1

Combinations of Progestin and Estrogen

| Progestin | Norethindrone Dose (mg) | Equivalent Dose (mg) | Estrogen | EE Equivalent Dose (mg) | Dose (mg) | P/E Ratio |
|---|---|---|---|---|---|---|
| Norethynodrel | 9.85 | 9.85 | Mestranol | 0.150 | 0.105 | 93.810 |
|  | 5.00 | 5.00 |  | 0.075 | 0.053 | 95.238 |
|  | 2.50 | 2.50 |  | 0.036 | 0.025 | 99.206 |
|  | 2.50 | 2.50 |  | 0.100 | 0.070 | 35.714 |
| Norethindrone | 10.00 | 10.00 | Mestranol | 0.060 | 0.042 | 238.095 |
|  | 2.00 | 2.00 |  | 0.100 | 0.070 | 28.571 |
|  | 1.00 | 1.00 |  | 0.050 | 0.035 | 28.571 |
|  | 1.00 | 1.00 |  | 0.080 | 0.056 | 17.857 |
| Norethindrone | 1.00 | 1.00 | Ethinyl estradiol (EE) | 0.050 | 0.050 | 20.000 |
|  | 1.00 | 1.00 |  | 0.035 | 0.035 | 28.571 |
|  | 0.50 | 0.50 |  | 0.035 | 0.035 | 14.286 |
|  | 0.40 | 0.40 |  | 0.035 | 0.035 | 11.429 |
| Norethindrone acetate | 2.50 | 2.50 | EE | 0.050 | 0.050 | 50.000 |
|  | 1.00 | 1.00 |  | 0.050 | 0.050 | 20.000 |
|  | 0.60 | 0.60 |  | 0.030 | 0.030 | 20.000 |
|  | 1.50 | 1.50 |  | 0.030 | 0.030 | 50.000 |
|  | 1.00 | 1.00 |  | 0.020 | 0.020 | 50.000 |
| Ethynodiol diacetate | 1.00 | 1.00 | Mestranol | 0.100 | 0.070 | 14.286 |
| Ethynodiol diacetate | 1.00 | 1.00 | EE | 0.050 | 0.050 | 20.000 |
|  | 1.00 | 1.00 |  | 0.035 | 0.035 | 28.571 |
| dl-Norgestrel | 0.50 | 0.75 | EE | 0.050 | 0.050 | 10.000 |
|  | 0.30 | 0.45 |  | 0.030 | 0.030 | 10.000 |
| Levonorgestrel | 0.10 | 0.35 | EE | 0.020 | 0.020 | 5.000 |
|  | 0.15 | 0.52 |  | 0.030 | 0.030 | 5.000 |

Equivalencies
50 mg Mestranol = approx. 35 mg Ethinyl estradiol (EE)
0.1 mg dl-Norgestrel = approx. 0.15 mg Norethindrone Each block in Table I describes a specific combination of progestin and estrogen, e.g., norethynodrel and mestranol, and within each block older combinations are listed first, with successively newer combinations following.

Suitable progestins for use in the present invention include, but are not limited to, natural and synthetic compounds having progestational activity, such as, for example, progesterone, levonorgestrel, norethindrone, norethindrone acetate, desogestrel, gestodene, dienogest, norgestimate, cyproterone acetate, norelgestromin, etonogestrel, ethynodiol diacetate, norgestrel, trimegestone, medroxyprogesterone acetate, chlormadinone acetate, drospirenone, and other natural and/or synthetic gestagens. Esters, conjugates, and prodrugs of suitable progestins can also be used.

The expression "prodrug" denotes a derivative of a known direct acting drug, which derivative has enhanced delivery characteristics and therapeutic value as compared to the drug and is transformed into the active drug by an enzymatic or chemical process. Ethynodiol diacetate, which is converted in vivo to norethindrone, is an example of a progestin prodrug that can be used in the present invention. Additional examples of progestin prodrugs include, but are not limited to, norgestimate (which is converted in vivo to 17-deacetyl norgestimate, also known as norelgestromin), desogestrel (which is converted in vivo to 3-keto desogestrel, also known as etonogestrel), and norethindrone acetate (which is converted in vivo to norethindrone).

Suitable estrogens in the present invention include, but are not limited to, natural and synthetic compounds having estrogenic activity, such as, for example, estradiol (17β-estradiol), 17α-estradiol, estriol; estrone, and their esters, such as the acetate, sulfate, valerate or benzoate esters of these compounds, including, for example, estradiol 17β-cypionate, estradiol 17-propionate, estradiol 3-benzoate, and piperazine estrone sulfate; ethinyl estradiol; conjugated estrogens (natural and synthetic); mestranol; agonistic anti-estrogens; and selective estrogen receptor modulators. Esters, conjugates and prodrugs of suitable estrogens can also be used. Examples of estrogen prodrugs that can be used in the present invention include, but are not limited to, estradiol acetate (which is converted in vivo to 17β-estradiol) and mestranol (which is converted in vivo to ethinyl estradiol).

In some aspects of the invention, the estrogen and progestin are administered for a period of 31 to 190 consecutive days. Each phase can be, but is not limited to, 7 to 84 days.

In some aspects of the invention, the estrogen and progestin are administered for a period of 39 to 61 days, of 42 to 60 days, of 45 to 57 days, or of 48 to 54 days. For example, the estrogen and progestin can be administered for a period of 49 days to 53 days. In some embodiments, the estrogen and progestin can be administered for a period of 49 days or 53 days. The first phase can be, but is not limited to, 7 to 21 days. The second phase can be, but is not limited to, 14 to 28 days.

The third phase can be, but is not limited to, 7 to 25 days. In some aspects of the invention, the first phase is 14 days, the second phase is 21 days, and the third phase is 14 days. In other aspects of the invention, the first phase is 14 days, the second phase is 21 days, and the third phase is 18 days.

In some embodiments, the first phase can be, but is not limited to, 7 to 21 days. The second phase can be, but is not limited to, 7 to 21 days. The third phase can be, but is not limited to, 14 to 32 days. In some aspects of the invention, the first phase is 14 days, the second phase is 14 days, and the third phase is 21 days. In other aspects of the invention, the first phase is 14 days, the second phase is 14 days, and the third phase is 25 days.

In some embodiments, the first phase can be, but is not limited to, 14 to 28 days. The second phase can be, but is not limited to, 7 to 21 days. The third phase can be, but is not limited to, 7 to 25 days. In some aspects of the invention, the first phase is 21 days, the second phase is 14 days, and the third phase is 14 days. In other aspects of the invention, the first phase is 21 days, the second phase is 14 days, and the third phase is 18 days In some aspects of the invention, the estrogen and progestin are administered for a period of 74 to 96 days, of 77 to 95 days, of 80 to 92 days, or of 83 to 89 days. For example, the estrogen and progestin can be administered for a period of 84 days to 88 days. In some embodiments, the estrogen and progestin can be administered for a period of 84 days or 88 days. The first phase can be, but is not limited to, 14 to 28 days. The second phase can be, but is not limited to, 14 to 28 days. The third phase can be, but is not limited to, 35 to 53 days. In some aspects of the invention, the first phase is 21 days, the second phase is 21 days, and the third phase is 42 days. In other aspects of the invention, the first phase is 21 days, the second phase is 21 days, and the third phase is 46 days.

In some embodiments, the first phase can be, but is not limited to, 14 to 28 days. The second phase can be, but is not limited to, 35 to 49 days. The third phase can be, but is not limited to, 14 to 32 days. In some aspects of the invention, the first phase is 21 days, the second phase is 42 days, and the third phase is 21 days. In other aspects of the invention, the first phase is 21 days, the second phase is 42 days, and the third phase is 25 days.

In some embodiments, the first phase can be, but is not limited to, 35 to 49 days. The second phase can be, but is not limited to, 14 to 28 days. The third phase can be, but is not limited to, 14 to 32 days. In some aspects of the invention, the first phase is 42 days, the second phase is 21 days, and the third phase is 21 days. In other aspects of the invention, the first phase is 42 days, the second phase is 21 days, and the third phase is 25 days.

In some aspects of the invention, the estrogen and progestin are administered for a period of 95 to 117 days, of 98 to 116 days, of 101 to 113 days, or of 104 to 110 days. For example, the estrogen and progestin can be administered for a period of 105 days to 109 days. In some embodiments, the estrogen and progestin can be administered for a period of 105 days or 109 days. The first phase can be, but is not limited to, 14 to 28 days. The second phase can be, but is not limited to, 35 to 49 days. The third phase can be, but is not limited to, 35 to 53 days. In some aspects of the invention, the first phase is 21 days, the second phase is 42 days, and the third phase is 42 days. In other aspects of the invention, the first phase is 21 days, the second phase is 42 days, and the third phase is 46 days.

In some aspects of the invention, the estrogen and progestin are administered for a period of 123 to 145 days, of 126 to 144 days, of 129 to 141 days, or of 132 to 138 days. For example, the estrogen and progestin can be administered for a period of 133 days to 137 days. In some embodiments, the estrogen and progestin can be administered for a period of 133 days or 137 days. The first phase can be, but is not limited to, 35 to 49 days. The second phase can be, but is not limited to, 42 to 56 days. The third phase can be, but is not limited to, 35 to 53 days. In some aspects of the invention, the first phase is 42 days, the second phase is 49 days, and the third phase is 42 days. In other aspects of the invention, the first phase is 42 days, the second phase is 49 days, and the third phase is 46 days.

In some aspects of the invention, the estrogen and progestin are administered for a period of 165 to 187 days, of 168 to 186 days, of 171 to 183 days, or of 174 to 180 days. For example, the estrogen and progestin can be administered for a period of 175 days to 179 days. In some embodiments, the estrogen and progestin can be administered for a period of 175 days or 179 days. The first phase can be, but is not limited to, 35 to 49 days. The second phase can be, but is not limited to, 56 to 70 days. The third phase can be, but is not limited to, 63 to 81 days. In some aspects of the invention, the first phase is 42 days, the second phase is 63 days, and the third phase is 70 days. In other aspects of the invention, the first phase is 42 days, the second phase is 63 days, and the third phase is 74 days.

In some aspects of the invention, the estrogen and progestin are administered for a period of 180 to 369 days, of 347 to 369 days, of 350 to 366 days, of 353 to 363 days, or of 356 to 362 days. For example, the estrogen and progestin can be administered for a period of 357 days to 361 days. In some embodiments, the estrogen and progestin can be administered for a period of 357 days or 361 days. The first phase can be, but is not limited to, 49 to 63 days. The second phase can be, but is not limited to, 168 to 182 days. The third phase can be, but is not limited to, 119 to 137 days. In some aspects of the invention, the first phase is 56 days, the second phase is 175 days, and the third phase is 126 days. In other aspects of the invention, the first phase is 56 days, the second phase is 175 days, and the third phase is 130 days. In some aspects of the invention, the estrogen and progestin are administered in four or more phases.

In some aspects of the invention, the method of providing an ascending-dose extended cycle regimen further includes a hormone-free period. The hormone-free period can be, but is not limited to, 2 to 10 consecutive days. The hormone-free period can be 2 to 8 consecutive days. For example, the hormone-free period can be 3, 5 or 7 days. The hormone-free period can be a non-administration or administration of a placebo. The hormone-free period can include administration of other active ingredients.

In some aspects of the invention, the method of providing an ascending-dose extended cycle regimen further comprises administering estrogen for a period of 2 to 10 consecutive days ("unopposed estrogen interval"). The unopposed estrogen interval can be for a period of 2 to 8 consecutive days. For example, administration of an ascending-dose extended cycle regimen can be followed by administration of the estrogen for a period of 3, 5 or 7 days. The unopposed estrogen interval can include administration of other active ingredients.

Examples of other additional pharmaceutically active ingredients or agents include, but are not limited to, vitamin D or vitamin D analogues; one or more of the B complex vitamins, such as vitamin B3 (niacin (i.e., nicotinic acid and/or nicotinamide)), vitamin B9 (folic acid or folate), vitamin B6 and/or vitamin B12; minerals such as, for example, calcium; iron (e.g., ferrous iron, such as, e.g., ferrous sulfate, ferrous fumarate, ferrous gluconate, or an iron glycine amino acid chelate); agents for preventing and treating bone conditions such as bisphosphonates alendronate), teriparatide (e.g., FORTEO™), and SERMs (selective estrogen receptor modulators, e.g., raloxifene).

These additional active agents can be administered during the period of administration of estrogen and progestin, the hormone-free period, the unopposed estrogen interval, or a combination of these periods. For example, vitamin D and/or calcium or a bisphosphonate can be administered during the hormone-free period as a method of maintaining or preventing loss of bone density. Suitable forms of vitamin D and of calcium and bisphosphonate would be known to those of skill in the art. The active ingredients can be provided in the same, different, or separate dosage forms.

In some aspects of the invention, the estrogen that is administered for a period of, e.g., 2 to 10 consecutive days is in a daily dosage that is the equivalent of 5 µg to 50 µg to 30 µg, or 10 µg of ethinyl estradiol.

The ascending-dose extended cycle regimens are optionally administered with an antidepressant. In some aspects of the invention, the antidepressant is administered in combination with estrogen during the unopposed estrogen interval of the regimen. In other aspects of the invention, the antidepressant is administered continuously throughout the regimen, or, in yet other aspects of the invention, the antidepressant is administered intermittently. For example, in some aspects of the invention, the antidepressant is administered intermittently during the late luteal phase, which is typically one to two weeks before menses. In yet other aspects of the invention, the antidepressant is administered one time during a menstrual cycle, or once weekly. For example, in some aspects of the invention, fluoxetine hydrochloride is administered in a one-time or once-weekly dose of about 90 mg. In other aspects of the invention, the antidepressant is administered during the hormone-free period.

The antidepressant that is optionally combined with the ascending-dose extended cycle regimens can be a selective serotonin reuptake inhibitor (SSRI), a selective serotonin and norepinephrine reuptake inhibitor (SSNRI), a tricyclic antidepressant or anxiolytic, or any antidepressant known to one of skill in the art. Suitable antidepressants include, but are not limited to, alprazolam (XANAX®), clomipramine (ANAFRANIL®), fluoxetine (PROZAC®), paroxetine (PAXIL®), sertraline (ZOLOFT®), nefazodone (SERZONE®), fenfluramine (PONDIMIN®) and venlafaxine (EFFEXOR®).

The daily amount of antidepressant administered can vary, depending on the antidepressant used, from about 0.75 to about 2 mg, from about 10 to about 20 mg, or from about 50 to about 100 mg. For example, in some aspects of the invention, fluoxetine hydrochloride is administered in a daily amount of about 5 mg to about 120 mg. A suitable daily amount of antidepressant for administration can be determined by one of skill in the art, e.g., a physician.

Thus, in some aspects of the invention, the method of providing an ascending-dose extended cycle regimen further comprises administering an antidepressant. The antidepressant can be administered (i) during a hormone-free period, (ii) in combination with an estrogen for a period of e.g., 2 to 10 consecutive days, (iii) continuously, (iv) intermittently, (v) one time, or (vi) once weekly. In some aspects of the invention, the antidepressant is a SSRI such as fluoxetine. In other aspects of the invention, the antidepressant is a SSNRI.

In some aspects of the invention, the administration of an ascending-dose extended cycle regimen of the present invention is followed by monophasic administration of an estrogen and a progestin. As used herein, "monophasic" refers to the continuous use of one particular dose of an estrogen and a progestin during the period of administration of the dosage form of the estrogen and progestin. In some aspects of the invention, the administration of an ascending-dose extended cycle regimen is followed by monophasic administration of an estrogen and a progestin continuously. In some aspects of the invention, the administration of an ascending-dose extended cycle regimen is followed by monophasic administration of an estrogen and a progestin for a period of greater than 30 or 31 consecutive days.

In some aspects of the invention, the administration of an ascending-dose extended cycle regimen is followed by monophasic administration of an estrogen and a progestin for a period of 350 to 370 consecutive days, of 260 to 280 consecutive days, of 175 to 190 consecutive days, or of 60 to 110 consecutive days. The monophasic administration of an estrogen and a progestin can be optionally followed either by a hormone-free period of, e.g., 2 to 10 consecutive days or by administration of estrogen for a period of, e.g., 2 to 10 consecutive days.

Treatment of Conditions and Disorders

An ascending-dose extended cycle regimen disclosed herein can be used as a method of female contraception. Thus, the invention is directed to a method of contraception in a female in need thereof by administering to the female an ascending-dose extended cycle regimen disclosed herein. The female can be, for example, of childbearing age or peri-menopausal.

However, an ascending-dose extended cycle regimen is also useful as a method of treating a variety of conditions and disorders in females. Thus, an ascending-dose extended cycle regimen can be used as a method of providing contraception to a female for the treatment of a condition or disorder, or as a method of providing contraception and treating a condition or disorder in a female. Such conditions and disorders are described below and include, but are not limited to: breakthrough bleeding; irregular withdrawal bleeding; menstrual bleeding disorders; symptoms associated with an ovarian cyst, uterine leiomyoma (fibroid tumor), and Polycystic Ovarian Syndrome; hirsutism; iron deficiency anemia; menstrual disorders; acne; endometriosis; endometrial cancer; ovarian cancer; benign breast disease; infections; ectopic pregnancy; temporomandibular disorder; catamenial symptoms; non-menstrual related headache, nausea, and depression; peri-menopausal symptoms; hypoestrogenism; menopausal disorders; and loss of bone density.

The invention, therefore, is also directed to a method of providing contraception to a female for treatment of a condition or disorder, wherein the female is in need of treatment for the condition or disorder, by administering to the female an ascending-dose extended cycle regimen disclosed herein. The female can be, for example, of childbearing age, peri-menopausal, or menopausal.

The invention is also directed to a method of providing contraception and treating a condition or disorder in a female, wherein the female is in need of both contraception and treatment of the condition or disorder, by administering to the female an ascending-dose extended cycle regimen disclosed herein. The female can be, for example, of childbearing age or peri-menopausal.

An ascending-dose extended cycle regimen disclosed herein includes administration to a female beginning at Day 1 of a menstrual cycle that is defined as beginning at the first day of menstrual flow. Alternatively, an ascending-dose extended cycle regimen disclosed herein can also include administration to a female beginning at Day 1 of a menstrual cycle that is defined as beginning with the day after the ending of the menstrual flow. Alternatively, an ascending-dose extended cycle regimen disclosed herein also can include administration to a female beginning at Day 1 of a menstrual cycle that is defined as beginning with any day within the menstrual cycle.

For each of the disclosed methods of the invention, the effect of administration of an ascending-dose extended cycle regimen, with respect to the specified condition (e.g., inducing the specified condition in the female, reducing the occurrence of the condition, minimizing the condition, or treating the condition or disorder) can be evaluated in comparison to each other, to the condition or disorder exhibited by the female after administration of a conventional or standard 28-day contraceptive regimen, after administration of an extended cycle contraceptive regimen other than an ascending-dose extended cycle regimen of the present invention, and/or with no contraceptive regimen. For example, the effect of administering an ascending-dose extended cycle regimen to treat a menstrual bleeding disorder can be evaluated by comparing the occurrence and/or severity of the bleeding disorder in females suffering from the disorder who have been administered an ascending-dose extended cycle regimen with the occurrence and/or severity of the bleeding disorder in females suffering from the disorder who have not been treated with a contraceptive regimen, or with females suffering from the disorder who have been administered a contraceptive regimen not disclosed in the present invention. The effect of administering an ascending-dose extended cycle regimen of the invention can also be evaluated by comparing the occurrence and/or severity of a condition in a female before and after administration of an ascending-dose extended cycle regimen of the invention, or by evaluating the condition of the female during the course of one or more cycles.

The present invention is directed to a method of reducing breakthrough bleeding in a female in need thereof by administering to the female an ascending-dose extended cycle regimen disclosed herein. The female can be, for example, of childbearing age or peri-menopausal.

The invention is also directed to a method of providing contraception and reducing breakthrough bleeding in a female in need thereof by administering to the female an ascending-dose extended cycle regimen disclosed herein. For example, the female can be of childbearing age or peri-menopausal.

The invention is directed to a method of inducing regular, predictable withdrawal bleeding in a female in need thereof by administering to the female an ascending-dose extended cycle regimen disclosed herein. The female can be, for example, of childbearing age or peri-menopausal. Administration of an ascending-dose extended cycle regimen is useful in controlling menstrual cycles in a female by inducing regular, predictable withdrawal bleeding. By suppressing ovulation and delivering estrogen and progesterone in a programmed fashion, an ascending-dose extended cycle regimen can establish or restore synchrony to the endometrium. This is particularly useful in the treatment of heavy or intermenstrual bleeding. The resulting predictable timing and shorter duration of bleeding are especially advantageous to peri-menopausal women, who often experience irregular menstrual cycles.

The invention is also directed to a method of providing contraception and inducing regular, predictable withdrawal bleeding in a female in need thereof by administering to the female an ascending-dose extended cycle regimen disclosed herein. The female can be, for example, a female of childbearing age or a peri-menopausal female.

The invention is directed to a method of reducing frequency or delaying onset of a menstrual cycle in a female in need of delayed or reduced menstruation by administering to the female an ascending-dose extended cycle regimen disclosed herein. The female can be, for example, of childbearing age or peri-menopausal. For example, particular groups or subpopulations of women can benefit from reduced menstruation, such as women enlisted in the U.S. military and women athletes. Control of the menstrual cycle, or even induction of amenorrhea using an ascending-dose extended cycle regimen, can be an advantage for women on active duty. The non-contraceptive benefits resulting from use of an ascending-dose extended cycle regimen, such as reduction in dysmenorrhea, premenstrual syndrome, menorrhagia, iron deficiency anemia, and ability to control timing of withdrawal bleeding, can be desirable and advantageous to women athletes as well. The term "amenorrhea" refers to the absence of bleeding during one or more menstrual cycles of a female. The term encompasses the absence of bleeding and/or spotting during the unopposed estrogen interval of an ascending-dose extended cycle regimen of the present invention when administered to a female, as well as the absence of bleeding or spotting throughout an entire menstrual cycle during administration of an ascending-dose extended cycle regimen.

The invention is also directed to a method of providing contraception and reducing frequency or delaying onset of a menstrual cycle in a female in need thereof by administering to the female an ascending-dose extended cycle regimen disclosed herein. The female can be, for example, a female of childbearing age or a peri-menopausal female.

The invention is directed to a method for minimizing uterine bleeding in a female in need thereof by administering to the female an ascending-dose extended cycle regimen disclosed herein. The female can be, for example, of childbearing age or peri-menopausal. By diminishing endometrial proliferation, administration of an estrogen and a progestin in an ascending-dose extended cycle regimen can reduce the volume and duration of menstrual flow. A female on a disclosed ascending-dose extended regimen can experience fewer total scheduled days of bleeding than a female on a traditional 28-day regimen, and can experience less blood loss, because an ascending-dose extended cycle regimen involves fewer stop/start transitions per year. The female to be treated can exhibit abnormal uterine bleeding, including, for example, menorrhagia. As used herein, "abnormal uterine bleeding" refers to an abnormal duration of bleeding (i.e., greater than 7 days of bleeding, or hypermenorrhea), abnormal amount of bleeding (i.e., greater than about 80 mL blood loss during menses, or menorrhagia), increased frequency of bleeding (i.e., less than 22 days between menstrual cycles, or polymenorrhea), or any combinations thereof.

The invention is also directed to a method of providing contraception and minimizing uterine bleeding in a female in need thereof by administering to the female an ascending-dose extended cycle regimen disclosed herein. The female can be, for example, a female of childbearing age or a peri-menopausal female.

The invention, moreover, is directed to a method of treating a menstrual bleeding disorder in a female in need thereof by administering to the female an ascending-dose extended cycle regimen disclosed herein. The female can be, for example, of childbearing age or peri-menopausal.

The invention is also directed to a method of providing contraception and treating a menstrual bleeding disorder in a female in need thereof by administering to the female an ascending-dose extended cycle regimen disclosed herein. The female can be, for example, a female of childbearing age or a peri-menopausal female.

The invention is directed to a method of treating symptoms associated with ovarian cysts, uterine leiomyomas (fibroids), or Polycystic Ovarian Syndrome in a female in need thereof by administering to the female an ascending-dose extended cycle regimen disclosed herein. The female can be, for example, of childbearing age, peri-menopausal, or menopausal. The invention is also directed to a method of providing contraception and treating symptoms associated with ovarian cysts, uterine leiomyomas (fibroids), or Polycystic Ovarian Syndrome in a female in need thereof by administering to the female an ascending-dose extended cycle regimen disclosed herein. The female can be, for example, a female of childbearing age or peri-menopausal.

Ovarian cysts, uterine leiomyomas (fibroids), or Polycystic Ovarian Syndrome can cause symptoms including, but not limited to, pelvic pain, dysmenorrhea, abnormal uterine bleeding, acne, and hirsutism. In the invention, such symptoms can be treated by administration of an ascending-dose extended cycle regimen described herein.

Ovarian cysts arise from functional cysts that commonly occur around mid-cycle, when a follicle destined to become an egg fails to mature. Instead of leaving the ovary in a process known as ovulation, it remains inside, floating in a tiny sac of fluid. It is that sac that eventually forms into a cyst. Although rarely malignant, ovarian cysts lead to 200,000 hospitalizations in the United States each year. For some women, some studies have shown that the cysts develop cycle after cycle. Though ovarian cysts can sometimes be asymptomatic, they can also cause pain (constant pelvic pain, pain during intercourse, pain during pelvic movement, and/or pain before or after menses), abnormal bleeding (lengthened, shortened, irregular and/or absent menses), and/or abdominal bloating or distension.

Uterine fibroids are benign growths of uterine muscle that sometimes exist singly, but most often are multiple and range in size from microscopic to filling most of the lower abdominal cavity. Many women with fibroids have no symptoms at all. For those that do, the most common complaints are pressure symptoms and heavy, prolonged periods. There may be pressure in the pelvic region from the enlarged uterus, and the resulting symptoms are often related to where the fibroid is exerting pressure (e.g., increased urinary frequency, constipation or difficulty with bowel movements). The pressure can also cause backache, lower abdominal discomfort, and pain during and after intercourse. Fibroids can cause very heavy and prolonged periods, leading to iron-deficiency anemia, as well as painful periods (secondary dysmenorrhea). The presence of fibroids can also cause reproductive problems such as infertility, multiple miscarriages, premature labor, or labor complications.

The term "ovarian cyst" as used above represents more singular occurrences caused by the failure of an egg to mature. Polycystic Ovarian Syndrome (PCOS), in contrast, is due to an abnormal production of LH (luteinizing hormone) and FSH (follicle stimulating hormone) by the pituitary gland. An imbalance of these hormones stops egg production and increases production of androgens, with the ovaries producing higher levels of testosterone and estrogens. This results in ovaries "peppered" with empty egg follicles that become inflamed cysts, irregular or stopped periods (which in turn causes infertility), excess body hair growth, and acne on the face and body. PCOS often leads to obesity, diabetes and hypertension.

Polycystic Ovarian Syndrome is the cause of most cases of androgen-dependent hirsutism. See Rittmaster, R. S., *Lancet* 349:191-195 (1997). Hirsutism can be described as the growth of excessive hair in women on parts of the body where excessive hair is generally not present, e.g., on the back and chest. Most cases of hirsutism are androgen-dependent, i.e., result from a combination of increased androgen production by the body and increased skin sensitivity to androgens. Normally, small quantities of androgens are produced by the ovaries and the adrenal glands. However, in women suffering from Polycystic Ovarian Syndrome, androgen levels are elevated, which can lead to the development of androgen-dependent conditions such as, for example, pronounced forms of acne (e.g., acne papulopustulosa), androgenetic alopecia and mild forms of hirsutism. Oral contraceptives can suppress the ovarian production of androgens and are thus useful in the treatment of these androgen-dependent conditions.

Thus, the invention is also directed to a method of treating hirsutism in a female in need thereof, by administering to the female an ascending-dose extended cycle regimen disclosed herein. The female can be, for example, of childbearing age, peri-menopausal, or menopausal.

The invention is also directed to a method of providing contraception and treating hirsutism in a female in need thereof, by administering to the female an ascending-dose extended cycle regimen disclosed herein. The female can be, for example, a female of childbearing age or peri-menopausal.

The invention is directed to a method of treating alopecia in a female in need thereof, by administering to the female an ascending-dose extended cycle regimen disclosed herein. The female can be, for example, of childbearing age, peri-menopausal, or menopausal. The invention is also directed to a method of providing contraception and treating alopecia in a female in need thereof, by administering to the female an ascending-dose extended cycle regimen disclosed herein. The female can be, for example, a female of childbearing age or peri-menopausal.

The invention is further directed to a method of decreasing risk of iron deficiency anemia in a female in need thereof by administering to the female an ascending-dose extended cycle regimen disclosed herein. The female can be, for example, of childbearing age or peri-menopausal. A reduction in the volume and duration of menstrual flow that can result from administration of, e.g., an ascending-dose extended cycle regimen can lead to a reduction in the total loss of blood, thus improving the body's iron stores and reducing the morbidity associated with menorrhagia. This effect is particularly desirable in women with coagulation disorders, for example, von Willebrand's disease. The female to be treated can be, but is not limited to, a peri-menopausal female.

The invention is also directed to a method of providing contraception and decreasing risk of iron deficiency anemia in a female in need thereof by administering to the female an ascending-dose extended cycle regimen disclosed herein. The female can be, for example, a female of childbearing age or a peri-menopausal female.

The invention is directed to a method of treating a menstrual disorder in a female in need thereof by administering to the female an ascending-dose extended cycle regimen disclosed herein. The female can be, for example, of childbearing age or peri-menopausal. Menstrual disorders include, but are not limited to, irregular menstrual cycles, dysmenorrhea (painful menstruation), mittelschmerz, and dysfunctional uterine bleeding, as well as premenstrual symptoms such as, but not limited to, those associated with premenstrual syndrome (PMS) or Premenstrual Dysphoric Disorder (PMDD).

The invention is also directed to a method of providing contraception and treating a menstrual disorder in a female in need thereof by administering to the female an ascending-dose extended cycle regimen disclosed herein. The female can be, for example, a female of childbearing age or a peri-menopausal female.

During the luteal phase of the menstrual cycle, as many as 75% of women with regular menstrual cycles experience some symptoms of premenstrual syndrome (PM), a recurring, cyclical disorder involving behavioral, emotional, social and physical symptoms (Steiner et al., *Annu. Rev. Med.* 48:447-455 (1997)). Behavioral, emotional and social symptoms include, but are not limited to, irritability, mood swings, depression, hostility and social withdrawal. Physical symptoms include, but are not limited to, bloating, breast tenderness, myalgia, migraines or headaches, and fatigue. True PMS only occurs during the luteal phase of the menstrual cycle, with a symptom-free period during the follicular phase. The etiology of PMS is still unknown.

A subgroup of women with PMS, about 2-9%, exhibit symptoms that are primarily related to a severe mood disorder. In these women, the diagnosis of Premenstrual Dysphoric Disorder (PMDD), which is defined in the Fourth edition of the Diagnostic and Statistical Manual of Mental Disorders (DSM-IV) can be applied. According to the DSM-IV, a woman with PMDD must have at least five premenstrual symptoms during the luteal phase, with at least one of the symptoms being an emotional or "core" symptom. The core symptoms must be irritability, anger, mood swings, tension or depression (and interfere with daily activities), and must be confirmed by a prospective daily rating for at least two cycles. Three to five percent of women with PMS report to have PMDD. There is also a subgroup of women who experience severe PMS, which accounts for about 20% of the PMS population. These women experience severe emotional symptoms that do not fall under the strict criteria of PMDD as defined in DSM-IV but require medical attention. U.S. application Ser. No. 10/309,313 relates to the use of estrogen/progestin contraceptive regimens optionally combined with an antidepressant for the treatment of PMS, PMDD, and related conditions.

Suppression of ovulation that can result from administration of the extended cycle regimen can also eliminate mid-cycle pain ("mittelschmerz") associated with rupture of the ovarian follicle. Additionally, suppression of ovulation and delivery of estrogen and progesterone in a regular, predictable schedule, which can result from use of an ascending-dose extended cycle regimen can be beneficial in the treatment of other menstrual disorders such as heavy or intermenstrual bleeding. In some aspects of the invention, the female can be a peri-menopausal female.

The invention is directed to a method of treating acne in a female in need thereof by administering to the female an ascending-dose extended cycle regimen disclosed herein. The female can be, for example, of childbearing age, peri-menopausal, or menopausal. An ascending-dose extended cycle regimen may suppress gonadotropin and decrease ovarian and adrenal androgen production, resulting in an improvement in acne of, e.g., women of childbearing age and older.

The invention is also directed to a method of providing contraception and treating acne in a female in need thereof by administering to the female an ascending-dose extended cycle regimen disclosed herein. The female can be, for example, a female of childbearing age or peri-menopausal.

The invention is directed to a method of treating endometriosis in a female in need thereof by administering to the female an ascending-dose extended cycle regimen disclosed herein. The female can be, for example, of childbearing age or peri-menopausal. The invention is also directed to a method of providing contraception and treating endometriosis in a female in need thereof by administering to the female an ascending-dose extended cycle regimen disclosed herein. The female can be, for example, a female of childbearing age or a peri-menopausal female.

In hormonal therapy of endometriosis, endometriotc tissue responds to adverse endocrine environments (low estrogen and/or high progestin concentration). Progestins produce marked atrophy of the endometrium and ectopic endometrial tissue and decrease intraperitoneal inflammation associated with endometriosis. The American College of Obstetrics and Gynecology stated that progestins, alone or in combination with estrogens as oral contraceptives, are an optimal choice for the management of endometriosis in women who desire contraception (American College of Obstetricians and Gynecologists, *ACOG Practice Bulletin No.* 11 (December 1999)). The use of an ascending-dose extended cycle regimen of the present invention can be beneficial for treating or preventing endometriosis.

Chronic pelvic pain often precedes and is associated with the development of endometriosis. Thus, the invention is also directed to a method of treating chronic pelvic pain in a female in need thereof by administering to the female an ascending-dose extended cycle regimen disclosed herein. The female can be, for example, of childbearing age or peri-menopausal. The invention is also directed to a method of providing contraception and treating chronic pelvic pain in a female in need thereof by administering to the female an ascending-dose extended cycle regimen disclosed herein. The female can be, for example, a female of childbearing age or a peri-menopausal female.

The invention is further directed to a method of reducing the risk of endometrial cancer in a female in need thereof by administering to the female an ascending-dose extended cycle regimen, disclosed herein. The female can be, for example, of childbearing age, peri-menopausal, or menopausal. The invention is also directed to a method of providing contraception and reducing the risk of endometrial cancer in a female in need thereof by administering to the female an ascending-dose extended cycle regimen disclosed herein. The female can be, for example, a female of childbearing age or peri-menopausal.

The invention is directed to a method of reducing the risk of ovarian cancer in a female in need thereof by administering to the female an ascending-dose extended cycle regimen disclosed herein. The female can be, for example, of childbearing age, peri-menopausal, or menopausal. The frequency of ovulation and thereby the frequency of ovarian stimulation can be reduced, suppressed, or eliminated by use of an ascending-dose extended cycle regimen. The invention is also directed to a method of providing contraception and reducing the risk of ovarian cancer in a female in need thereof by administering to the female an ascending-dose extended cycle regimen disclosed herein. The female can be, for example, a female of childbearing age, peri-menopausal, or menopausal.

The invention is further directed to a method of treating benign breast disease, including, but not limited to, fibrocystic breast disease, in a female in need thereof by administering to the female an ascending-dose extended cycle regimen disclosed herein. The female can be, for example, of childbearing age, peri-menopausal, or menopausal. About a third of all women between the ages of 30 and 50 will be diagnosed with fibrocystic breast disease or other benign breast condition. Other terms for this condition include chronic mastitis (inflammation) and mammary dysplasia.

The invention is also directed to a method of providing contraception and treating benign breast disease in a female in need thereof by administering to the female an ascending-dose extended cycle regimen disclosed herein. The female can be, for example, a female of childbearing age or peri-menopausal.

The invention is also directed to a method of reducing the risk of colorectal cancer in a female in need thereof by administering to the female an ascending-dose extended cycle regimen disclosed herein. The female can be, for example, of childbearing age, peri-menopausal, or menopausal. An ascending-dose extended cycle regimen of the present invention is thought to protect against colorectal cancer as a result of changes in bile synthesis and secretion due to the female hormones in the regimen, which is thought to lead to a reduced concentration of bile acids in the colon. It has also been observed that estrogen inhibits the growth of colon cancer cells in vitro, and estrogen receptors have been identified in normal and neoplastic colon epithelial cells. See Fernandez, E., et al., *British J. Cancer* 84:722-727 (2001). Thus, an ascending-dose extended regimen can be beneficial in the prevention or reduction in the occurrence of colorectal cancer.

The invention is also directed to a method of providing contraception and reducing the risk of colorectal cancer in a female in need thereof by administering to the female an ascending-dose extended cycle regimen disclosed herein. The female can be, for example, a female of childbearing age or peri-menopausal.

The invention is directed to a method of preventing or treating an infection in a female in need thereof by administering to the female an ascending-dose extended cycle regimen disclosed herein. The female can be, for example, of childbearing age, peri-menopausal, or menopausal. For example, sexually transmitted diseases (STDs) are infections caused by a pathogen such as a virus, bacterium, parasite, or fungus, that is spread from person to person through sexual contact. STDs can be painful, irritating, and even life-threatening. An ascending-dose extended cycle regimen is believed to have a protective role against the development of some STDs because it stimulates the body to produce a thicker cervical mucous, which acts as a barrier to semen carrying bacteria that cause sexually transmitted diseases.

The invention is also directed to a method of providing contraception and treating an infection in a female in need thereof by administering to the female an ascending-dose extended cycle regimen disclosed herein. The female can be, but is not limited to, a female of childbearing age or peri-menopausal.

Pelvic Inflammatory Disease (ND) is a complication that can result from STD infections. PID is a serious syndrome of the female reproductive tract that results from the spread of infections (most often sexually transmitted infections such as *Chlamydia trachomatis* and *Nisseris gonnorrheoea*) from the vagina and endocervix to the uterus, fallopian tubes and ovaries. PID is commonly manifested as endometritis (infection of the lining of the uterus) or salpingitis (infection of the fallopian tubes), and less commonly as pelvic peritonitis and/or inflammation of contiguous structures. (MacDonald, N. E., and Bowie, W. R., *Canadian Communicable Disease Report* 21S4: 25-33 (1995); Westrom, L. and Mardh, P-A., *Sexually Transmitted Diseases*, $2^{nd}$ Ed., pages 593-613, New York: McGraw-Hill, 1990).

PID is a major cause of infertility and ectopic pregnancy. Ectopic pregnancy results from the implantation of a fertilized ovum in the fallopian tube or in the abdominal cavity and is thought to be caused by ciliary dysfunction within the fallopian tube resulting from prior tubal infection with *N. gonorrhoea* and/or *C. trachomatis*, which often results in loss of ciliated epithelial cells from the fallopian tubes. It has been estimated that prior tubal infection with STD agents causes about 50% of the cases of ectopic pregnancy, (MacDonald. N. E., and Brunham, R., *Canadian Journal of Human Sexuality* 6(2):161-170 (1997).)

An ascending-dose extended cycle regimen is believed to have a protective role against the development of PID because it stimulates the body to produce thicker cervical mucous, which helps prevent semen carrying STD-causing bacteria from gaining access to the uterus and eventually causing PID and PID-related complications, such as ectopic pregnancy.

Thus, an ascending-dose extended cycle regimen of the present invention can be useful in the prevention or reduction in occurrence of sexually transmitted diseases, Pelvic Inflammatory Disease, and ectopic pregnancy. Accordingly, the invention is directed to a method of preventing or reducing the occurrence of a sexually transmitted disease or Pelvic Inflammatory Disease in a female in need thereof by administering to the female an ascending-dose extended cycle regimen disclosed herein. The invention is also directed to a method of preventing ectopic pregnancy in a female in need thereof by administering to the female an ascending-dose extended cycle regimen disclosed herein. The female can be, but is not limited to, a female of childbearing age or a peri-menopausal female.

The invention is also directed to a method of providing contraception and treating a sexually transmitted disease or Pelvic Inflammatory Disease in a female in need thereof by administering to the female an ascending-dose extended cycle regimen disclosed herein. The invention, moreover, is directed to a method of providing contraception and preventing ectopic pregnancy in a female in need thereof by administering to the female an ascending-dose extended cycle regimen disclosed herein. The female can be, but is not limited to, a female of childbearing age or a peri-menopausal female.

In addition, use of an ascending-dose extended cycle regimen, in comparison to the use of a conventional 28-day contraceptive regimen, can lead to a reduction in the reported occurrences of infection such as urinary tract infections, pharyngitis, upper respiratory tract infections, and sinusitis. Thus, the invention is further directed to the prevention or reduction in occurrence of certain infections, such as urinary tract infections, pharyngitis, upper respiratory tract infections, and sinusitis, in a female in need thereof by administering to the female an ascending-dose extended cycle regimen disclosed herein. The female can be, for example, of childbearing age, peri-menopausal, or menopausal. The invention is also directed to a method of providing contraception and treating certain infections, such as urinary tract infections, pharyngitis, upper respiratory tract infections, and sinusitis, in a female in need thereof by administering to the female an ascending-dose extended cycle regimen disclosed herein. The female can be, for example, of childbearing age or peri-menopausal.

The invention is also directed to a method of treating temporomandibular disorder in a female in need thereof by administering to the female an ascending-dose extended cycle regimen disclosed herein. The female can be, for example, of childbearing age, peri-menopausal, or menopausal. Temporomandibular disorders (TMD) are disorders of the jaw muscles, temporomandibular joints, and/or the nerves associated with chronic facial pain. An ascending-dose extended cycle regimen of the present invention can be useful in the treatment of TMD. The invention is also directed to a method of providing contraception and treating temporomandibular disorder in a female in need thereof by administering to the female an ascending-dose extended cycle regimen disclosed herein. The female can be, for example, of childbearing age or peri-menopausal.

The invention is directed to a method of treating a catamenial symptom in a female in need thereof by administering to the female an ascending-dose extended cycle regimen disclosed herein. The female can be, for example, of childbearing age or peri-menopausal. Catamenial symptoms are those associated with conditions, disorders, or diseases that can worsen around the time of menses. Such conditions, disorders, or diseases include, but are not limited to, asthma, rheumatoid arthritis, migraine headaches, seizure disorders or epilepsy, multiple sclerosis, and diabetes. The invention is also directed to a method of providing contraception and treating a catamenial symptom in a female in need thereof by administering to the female an ascending-dose extended cycle regimen disclosed herein. The female can be, for example, of childbearing age or peri-menopausal.

Arthritis is a prevalent chronic condition in women. Hormonal factors can influence the frequency and severity of arthritis. In some women, arthritis symptoms such as joint stiffness, swelling and pain peak during the postovulatory phase of the menstrual cycle, and cyclic changes in local antibody release, white blood cell subpopulations and altered pain perception have been proposed as possible mechanisms (Case, A. M. and Reid, R. L., *Arch. Intern. Med.* 158:1405-1412 (1998)). Estrogen administered as a single agent, and as part of a combined oral contraceptive has been reported to benefit some women (Kay, C. R. and Wingrave, S. J., *Lancet* 1:1437 (1983); Linos, A., et al., *Lancet* 1:1871 (1978)). Thus, use of an ascending-dose extended cycle regimen can be beneficial as a method of treating a catamenial symptom, such as, e.g., a symptom associated with rheumatoid arthritis, in a female in need thereof.

Approximately 60% of women with migraines report a relationship to menstruation (Case, A. M. and Reid, R. L., *Arch. Intern. Med.* 158:1405-1412 (1998)). Decreasing levels of estrogen during the late luteal phase of the menstrual cycle or abrupt withdrawal of estrogen as during the non-administration period in women taking oral contraceptives are thought to trigger migraine attacks (Sulak P. J., et al., *Obstet. Gynecol* 95:261-266 (2000); Kudrow, L., *Headache* 15:36-49 (1975); Whtty, C. W. M., et al., *Lancet* 1:856-859 (1966)). Thus, use of an ascending-dose extended cycle regimen can be beneficial as a method of treating a catamenial symptom in a female in need thereof, such as, e.g., a migraine headache in a female.

Catamenial epilepsy refers to seizure disorders that occur or worsen around menstruation. It is believed to result from cyclic alterations in both ovarian hormone levels and drug metabolism (Case, A. M. and Reid, R. L., *Arch. Intern. Med.* 158:1405-1412 (1998)). Thus, use of an ascending-dose extended cycle regimen can be beneficial as a method of treating a catamenial symptom such as, e.g., a symptom associated with epilepsy, in a female in need thereof.

The invention is directed to a method of treating headache or nausea unrelated to the menstrual cycle in a female in need thereof by administering to the female an ascending-dose extended cycle regimen disclosed herein. The female can be, for example, of childbearing age, peri-menopausal, or menopausal. Use of an ascending-dose extended cycle regimen, in comparison to the use of a conventional 28-day contraceptive regimen, can lead to a reduction in the reported occurrences of non-menstrual-related headache and nausea. Thus, a disclosed ascending-dose extended cycle regimen can be used as a method of preventing or treating non-menstrual-related headache and nausea. The invention is also directed to a method of providing contraception and treating headache or nausea unrelated to the menstrual cycle in a female in need thereof by administering to the female an ascending-dose extended cycle regimen disclosed herein. The female can be, for example, of childbearing age or peri-menopausal.

The invention is directed further to a method of treating depression unrelated to the menstrual cycle in a female in need thereof by administering to the female an ascending-dose extended cycle regimen disclosed herein. The female can be, for example, of childbearing age, peri-menopausal, or menopausal. "Depression" is a term that is often used to refer to different forms of depressive disorders and includes major depression, bipolar disorder (sometimes called manic-depressive illness), and dysthymia, a less severe form of depression. Major depression is manifested by a combination of symptoms that interfere with the ability to work, study, sleep, eat and enjoy once pleasurable activities. Bipolar disorder, which is not nearly as prevalent as other forms of depressive disorders, is characterized by cycling mood changes. Dysthymia, a less severe type of depression, involves long-term, chronic symptoms that do not disable, but keep one from functioning well or from feeling well. "Depression" also includes the less severe, temporary sadness and loneliness often felt from time to time. Use of an ascending-dose extended cycle regimen, compared to use of a conventional 28-day contraceptive regimen, can lead to a reduction in the reported occurrences of non-menstrual-related depression. Thus, a disclosed ascending-dose extended regimen can be used as a method of preventing or treating non-menstrual-related depression.

The invention is also directed to a method of providing contraception and treating depression unrelated to the menstrual cycle in a female in need thereof by administering to the female an ascending-dose extended cycle regimen disclosed herein. The female can be, for example, of childbearing age or peri-menopausal.

The invention is further directed to a method of increasing contraceptive effectiveness in a female in need thereof by administering to the female an ascending-dose extended cycle regimen disclosed herein. The female can be, but is not limited to, a female of childbearing age or a peri-menopausal female. A female in need of contraceptive effectiveness can be, but is not limited to, a higher weight female. A "higher weight female" refers to a human female weighing about 70 kg or more or having a body mass index (BMI) of greater than about 25. In a recent study of body weight and oral contraceptive failure, women weighing about 70.5 kg or more were reported to have a 60% higher risk of oral contraceptive failure (Holt, V. L., et al., *Obstet. Gynecol.* 99:820-827 (2002)).

Thus, the invention is directed to a method of increasing contraceptive effectiveness in a higher-weight female in need thereof, by administering to the female an ascending-dose extended cycle regimen disclosed herein. The invention is directed to a method of increasing the contraceptive effectiveness in a human female weighing about 70 kg or more, weighing about 80 kg or more, or weighing about 90 kg or more, by administering to the female an ascending-dose extended cycle regimen.

A disclosed ascending-dose extended cycle regimen can also be used as a method of increasing the contraceptive effectiveness in a human female with a body mass index of greater than about 25, greater than about 30, or greater than about 35. Thus, the invention is also directed to a method of increasing the contraceptive effectiveness in a human female with a body mass index of greater than about 25, greater than about 30, or greater than about 35, by administering to the female an ascending-dose extended cycle regimen.

The invention is also directed to a method of increasing fertility in a female in need thereof, by administering to the female an ascending-dose extended cycle regimen disclosed herein, followed by discontinuation of the regimen and optional administration of an agent to induce ovulation in the female. The female can be, but is not limited to, a female of childbearing age or a peri-menopausal female.

It has been observed clinically that women who are taking oral contraceptives for anovulation often conceive when pills are missed, or shortly after discontinuing oral contraceptive treatment, most likely due to a "rebound effect" occurring in the ovary at least for a short period of time. Suppression of ovarian activity using oral contraceptive pills for 2-6 months may result in decreases in early follicular ovarian androgen production and LH and estradiol levels. Increased androgen levels have been shown to have adverse effects on folliculogenesis. These endocrine changes in the early follicular phase may be responsible for improved ovarian response to clomiphene or other treatments for anovulatory infertility. See Brannigan, E. F., and Estes, M. A., *Am. J. Obstet. Gynecol.* 188:1424-1430 (2003).

Examples of agents that induce ovulation, and that can be administered following discontinuation of an ascending-dose extended cycle regimen of the present invention, include, but are not limited to, menotropins (Follicle Stimulating Hormone (FSH) and Luteinizing Hormone (LH), e.g., Pergonal®) and chlomiphene citrate (Clomid®). The ovulation-inducing agent can be administered during a suitable time as can be determined by one of skill in the art, e.g., a physician. In some aspects of the invention, the ovulation-inducing agent can be administered, e.g., within about one week to about one month, or within about one week to about two weeks, after discontinuation of an ascending-dose extended cycle regimen of the present invention. In some aspects of the invention, the ovulation-inducing agent is administered, e.g., 2 to 10 days, or 5 to 9 days after discontinuation of an ascending-dose extended cycle regimen.

Thus, the invention is directed to a method of increasing fertility in a female in need thereof, the method comprising (i) administration to the female of an ascending-dose extended cycle regimen disclosed herein; (ii) discontinuation of administration of an ascending-dose extended cycle regimen; and (iii) optional administration to the female of an ovulation-inducing agent during the discontinuation of administration of an ascending-dose extended cycle regimen; wherein fertility in the female is increased.

In some aspects of the invention, the disclosed methods are particularly useful in peri-menopausal women and/or menopausal women. Peri-menopausal and menopausal women frequently experience a large variety of conditions and disorders that have been attributed to estrogen deprivation due to ovarian failure or hypoestrogenism. The duration of these disorders can be extremely variable and include hot flushes which can be devastating in some women and very mild in others. Dryness of the vagina associated with susceptibility to minor infections, and frequently associated with discomfort during intercourse, is another symptom that can be directly related to the decrease in estrogen availability.

In a long-term sense, one of the most health-threatening aspects of menopause is the loss of mineral from bone which can result in a decrease in bone mass (osteoporosis) and generates a serious risk of fractures. For example, evidence exists that there is a six-fold increase in fractures in post-menopausal women as opposed to men of the same age (Garraway et al., *Mayo Clinic Proceedings* 54:701-707 (1979)). These fractures, of course, carry a high complication rate among older people, a marked increase in disability and general morbidity, and certainly an increased risk of mortality.

Another serious health-threatening aspect of menopause is the impressive loss of protection against heart attacks, which is enjoyed by younger women up to the age of 60, when compared to men of the same age. The steep increase in mean serum cholesterol concentration, which occurs around menopause (during the fourth and fifth decades), can contribute importantly to the progressive increase in death from ischemic heart disease in older women. In the eighth and ninth decades, the incidence of deaths from ischemic heart disease, approaches that of men (Havlik, R. J. and Manning-Feinleid, P. H., NIH Publication No. 79-1610, U.S. Department of HEW (1979)).

Accordingly, the invention is directed to a method for treating conditions, such as the physical conditions described above, resulting from menopausal estrogen decline in a menopausal female by administering an ascending-dose extended cycle regimen disclosed herein to the female. The invention is also directed to a method for treating conditions, such as the physical conditions described above, resulting from hypoestrogenism in a female by administering an ascending-dose extended cycle regimen disclosed herein to the female. The invention is further directed to a method for treating conditions, such as the physical conditions described above, resulting from ovarian failure in a female by administering an ascending-dose extended cycle regimen disclosed herein to the female.

The invention is also directed to a method of providing contraception and treating conditions, such as the physical conditions described above, resulting from hypoestrogenism in a peri-menopausal female in need thereof by administering an ascending-dose extended cycle regimen disclosed herein to the peri-menopausal female. The invention is further directed to a method of providing contraception and treating conditions, such as the physical conditions described above, resulting from ovarian failure in a peri-menopausal female in need thereof by administering an ascending-dose extended cycle regimen disclosed herein to the peri-menopausal female.

In addition to the above-mentioned major physical problems, some menopausal and peri-menopausal women experience a large variety of other symptoms ranging from depression, insomnia, and nervousness, to symptoms of arthritis and so forth.

It is generally agreed that estrogen is the most effective agent for the control or prevention of menopausal flushes and vaginal atrophy. It is effective in retarding or preventing the appearance of clinical evidence of osteoporosis. In appropriate doses, when combined with progestin, a favorable effect upon blood lipids can also be seen. Problems with estrogen therapy do exist, however, and have been widely explored and documented in the medical literature. The means by which estrogen has been administered, generally speaking, involves either the use of estrogen alone or estrogen plus a progestin.

Estrogen alone, given in small doses on a continuous basis, is effective in most patients for the control of the above symptoms and problems associated therewith. However, although the vast majority of women taking continuous low-dose estrogen will not have bleeding for many months or even years, there is a distinct risk posed by this routine of silently (i.e., exhibiting no overt symptoms) developing "hyperplasia of the endometrium." This term refers, of course, to an overstimulation of the lining of the uterus which can become pre-malignant, coupled with the possibility that the patient will eventually develop cancer of the uterine lining even under such a low-dose regimen (Gusberg et al., *Obstetrics and Gynaecology* 17:397-412 (1961)).

Estrogen alone can also be given in cycles, usually 21-25 days on treatment and 5-7 days off treatment. Again, if small doses of estrogen are required to control the symptoms and it is used to this fashion, only about 10% of women will experience withdrawal bleeding between the cycles of actual treatment. However, one must again be concerned by the risk of developing endometrial hyperplasia and by the increased relative risk of developing cancer of the uterus (Research on the Menopause: Report of a W.H.O. Scientific Group, 53-68 (1981)).

The addition of progestin with estrogen, however, as in an ascending-dose extended cycle disclosed herein, will virtually eliminate the concern about developing endometrial hyperplasia and reduce the risk of developing endometrial carcinoma below that of the untreated general population.

Thus, the invention is directed to a method of treating a menopausal disorder or a peri-menopausal disorder or symptom in a female in need thereof by administering to the female an ascending-dose extended cycle regimen disclosed herein. The invention is also directed to a method of providing contraception and treating a peri-menopausal disorder or symptom in a peri-menopausal female in need thereof by administering to the female an ascending-dose extended cycle regimen disclosed herein.

An ascending-dose extended cycle regimen can be used as a method of maintaining bone density or preventing loss of bone density in a female. An ascending-dose extended cycle regimen can also be used in this way by administering calcium and/or vitamin D, e.g., in combination with the administration of an estrogen and a progestin.

An ascending-dose extended cycle regimen is not limited to administration to peri-menopausal or menopausal females as a method of maintaining bone density or preventing bone loss. An ascending-dose extended cycle regimen can also be used in a method of maintaining bone density or preventing bone loss by administration to a female of childbearing age that is not peri-menopausal or menopausal. For example, an ascending-dose extended cycle regimen can be used with females 12-16 years of age who have not yet achieved peak bone density, but who, due to various conditions such as anorexia, are at risk of loss of bone density or at risk of not achieving a normal physiologic bone density for age and developmental maturity.

Thus, an ascending-dose extended cycle regimen can also be used as a method of treating a condition resulting from menopausal or peri-menopausal estrogen decline, including osteoporosis. An ascending-dose extended cycle regimen can also be used as a method of providing contraception and treating a condition in a peri-menopausal female in need thereof resulting from peri-menopausal estrogen decline, including osteoporosis.

An ascending-dose extended cycle regimen can also be used as a method of treating a female in need of hormone replacement therapy.

Modes of Administration and Compositions

The estrogen and/or progestin are administered in the conventional manner by any route where they are active. For example, administration can be by, but is not limited to, oral, parenteral, subcutaneous, intravenous, intramuscular, intraperitoneal, transdermal, buccal, or ocular routes, or intravaginally, by inhalation, by depot injections, or by hormone implants. Thus, the dosage forms for the estrogen anti/or progestin (either alone or in combination with other pharmaceuticals) can be, but are not limited to, sublingual, injectable (including short-acting, depot, implant and pellet forms injected subcutaneously or intramuscularly), vaginal creams, suppositories, pessaries, rings, rectal suppositories, intrauterine devices, and transdermal forms such as patches and creams.

Thus, pharmaceutical compositions containing the estrogen and/or progestin and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder. It is known in the art that the active ingredients can be contained in such compositions with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modern Pharmaceutics", Banker & Rhodes, Marcel Dekker, Inc. 1979; and "Goodman & Gilman's The Pharmaceutical Basis of Therapeutics," $6^{th}$ Edition, MacMillan Publishing Co., New York 1980 can be consulted.

For oral administration, the estrogen and/or progestin can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

The pharmaceutical compositions of the estrogen and/or progestin also can comprise suitable solid or gel phase carriers or excipients such as calcium carbonate, calcium phosphate, various sugars, starches, cellulose derivatives, gelatin, and polymers such as, e.g., polyethylene glycols.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All compositions for oral administration should be in dosages suitable for such administration.

For buccal administration, the estrogen and progestin compositions can take the form of tablets or lozenges formulated in conventional manner.

For administration by inhalation, the estrogen and/or progestin for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The estrogen and/or progestin can be formulated for parenteral administration by injection, e.g., by bolus injection or continuous infusion. The compounds can be administered by continuous infusion subcutaneously over a period of about 15 minutes to about 24 hours. Compositions for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

The estrogen and/or progestin can also be formulated in rectal compositions such as suppositories or retention enemas, e.g., containing conventional suppository bases such as cocoa butter or other glycerides.

In addition to the compositions described previously, the estrogen and/or progestin can also be formulated as a depot preparation. Such long acting compositions can be administered by implantation (e.g., subcutaneously or intramuscularly) or by intramuscular injection. Depot injections can be administered at about 1 to about 6 months or longer intervals. Thus, for example, the estrogen and/or progestin can be formulated with suitable polymeric or hydrophobic materials (e.g., as an emulsion in an acceptable oil) or ion exchange resins, or as sparingly soluble derivatives, for example, as a sparingly soluble salt.

For transdermal administration, the estrogen and/or progestin can be applied by any transdermal, therapeutic system that is consequently supplied to the organism, such as, for example, as a transdermal patch, transdermal cream or plaster. For example, the estrogen and/or progestin can be formulated as a transdermal patch. The preparation and use of transdermal patches are well known to those of skill in the art and are available in different designs, including matrix-type or reservoir-type designs. In addition to the estrogen and/or progestin, transdermal patches can contain additional components such as penetration-enhancing agents and/or additional excipients that are conventionally employed, such as, e.g., carriers, gelling agents, suspending agents, dispersing agents, preservatives, stabilizers, wetting agents, emulsifying agents, and the like.

For vaginal administration, the estrogen and/or progestin can be formulated as vaginal gels, creams, tampons, suppositories, vaginal rings, intrauterine devices and the like. The preparation of each of these formulations is well known to those of skill in the art.

The estrogen and/or progestin can also be administered with other active ingredients. The hormone-free period or the unopposed estrogen interval can also include administration of other active ingredients. For example, as described above, estrogen and/or progestin can be administered in combination with an antidepressant. Estrogen and/or progestin can also be administered with vitamin D and/or calcium in the ascending-dose extended cycle regimens as a method of maintaining or preventing loss of bone density. Alternatively, vitamin D and/or calcium can be administered in the ascending-dose extended cycle regimens during the unopposed estrogen interval following administration of estrogen and/or progestin. The form of vitamin D and of calcium used in the present invention would be well known to those of skill in the art, as would the amount. For example, calcium can be administered in the form of calcium carbonate, at a dosage level of e.g., 500 mg.

In some aspects of the invention, the estrogen and/or progestin are in a oral, transdermal, intravaginal, implantable pellet, or injectable liquid dosage form. For example, the estrogen and/or progestin can be in an oral dosage form, a transdermal dosage form, or an intravaginal dosage form.

In some aspects of the invention, the estrogen and progestin can be combined in one dosage form. In other aspects of the invention, the estrogen and progestin can be provided in different or separate dosage forms. Similarly, other active ingredients can be provided in the same, different, or separate dosage forms.

In some aspects of the invention, each phase of the regimen of the invention can be administered in a separate, single dosage form. In other aspects of the invention, each phase of the regimen of the invention can be administered in one or more separate dosage forms. For example, each phase can be administered using a separate ring or transdermal device (such as a patch). As another example, each phase can be administered using one or more rings or transdermal devices.

The present invention also provides a combination of two or more modes of administration with each regimen. For example, the estrogen can be provided by transdermal administration and the progestin can be provided by vaginal administration. As another example, the estrogen can be provided by transdermal administration, the progestin can be provided by transdermal administration, and an SSRI can be provided by oral administration.

Kits and Patient Education

The dosages or compositions for the ascending-dose extended cycle regimens of the invention can be provided in the form of a kit or package, with the dosages arranged for proper sequential administration. For example, in the oral form of the composition, the present invention provides a pharmaceutical package which contains combination-type contraceptives in multiple dosage units in a synchronized, fixed sequence, wherein the sequence or arrangement of the dosage units corresponds to the stages of daily administration.

Thus, for example, the pharmaceutical compositions useful in the Invention can be provided in kit form containing greater than 30 or 31 tablets intended for ingestion on successive days. In some embodiments, the kit further contains, e.g., 2 to 10 tablets, intended for ingestion on successive days following the ingestion of the greater than 30 or 31 tablets. Administration is daily for a period of greater than 30 or 31 consecutive days using tablets containing both the estrogen and the progestin, and, in some embodiments, is followed by administration that is daily for, e.g., 2 to 10 consecutive days using either placebo tablets or tablets containing estrogen. For example, administration can be for 40-190 consecutive days, using tablets containing both estrogen and the progestin, followed by administration for, e.g., at least 2-10 days with estrogen, using tablets containing estrogen. As another example, administration can be for 75-95 days, using tablets containing both an estrogen and a progestin, followed by administration for, e.g., at least 2-10 days with estrogen, using tablets containing estrogen. As yet another example, administration can be for 168-186 days, using tablets containing both an estrogen and a progestin, followed by administration for, e.g., at least 2-10 days with estrogen, using tablets containing estrogen.

Some aspects of the invention provide a pharmaceutical kit comprising a first oral dosage capable of providing a daily dosage of estrogen and a daily dosage of progestin; a second oral dosage capable of providing a daily dosage of estrogen that is equal to or higher than that of the first oral dosage and capable of providing a total daily dosage of estrogen and progestin that is higher than that of the first oral dosage; and a third oral dosage capable of providing a daily dosage of estrogen that is equal to or higher than that of the second oral dosage and capable of providing a total daily dosage of estrogen and progestin that is higher than that of the second oral dosage; wherein the oral dosages are capable of providing estrogen and progestin for a period of greater than 30 or 31 consecutive days.

Other aspects of the invention provide a pharmaceutical kit comprising a first oral dosage capable of providing a daily dosage of estrogen and a daily dosage of progestin; a second oral dosage capable of providing a total daily dosage of estrogen and progestin that is higher than that of the first oral dosage and capable of providing a daily dosage of progestin that is less than twice that of the first oral dosage; wherein the oral dosages are capable of providing estrogen and progestin for a period of greater than 42 consecutive days. In some aspects of the invention, the second oral dosage is capable of providing a daily dosage of estrogen that is equal to or higher than that of the first oral dosage. In some aspects of the invention, the pharmaceutical kit includes greater than 30 or 31 oral daily dosages.

In some embodiments, a pharmaceutical kit of the present invention comprises 14 to 28 first oral dosages, 14 to 28 second oral dosages, and 35 to 53 third oral dosages. For example, a pharmaceutical kit of the present invention can contain 21 first oral dosages, 21 second oral dosages, and 42 third oral dosages.

In some embodiments, a pharmaceutical kit of the present invention comprises 14 to 28 first oral dosages, 35 to 49 second oral dosages, and 14 to 32 third oral dosages. For example, a pharmaceutical kit of the present invention can contain 21 first oral dosages, 42 second oral dosages, and 21 third oral dosages.

In some embodiment, a pharmaceutical kit of the present invention comprises 35 to 49 first oral dosages, 14 to 28 second oral dosages, and 14 to 32 third oral dosages. For example, a pharmaceutical kit of the present invention can contain 42 first oral dosages, 21 second oral dosages, and 21 third oral dosages.

In some embodiments, the first oral dosage is capable of providing 20 µg of ethinyl estradiol and 150 µg of levonorgestrel, the second oral dosage is capable of providing 25 µg of ethinyl estradiol and 150 µg of levonorgestrel, and the third oral dosage is capable of providing 30 µg of ethinyl estradiol and 150 µg of levonorgestrel.

The pharmaceutical kits of the present invention can further contain a fourth oral dosage capable of providing estrogen. In some embodiments, the fourth oral dosage comprises a daily equivalent of 10 µg of ethinyl estradiol. In some embodiments, a pharmaceutical kit according to the present invention comprises 2 to 10 fourth oral dosages. For example, a pharmaceutical kit of the present invention can contain 3 or 7 fourth oral dosages.

Some aspects of the invention provide a pharmaceutical kit comprising a first vaginal ring capable of providing a daily dosage of estrogen and a daily dosage of progestin; a second vaginal ring capable of providing a daily dosage of estrogen that is equal to or higher than that of the first vaginal ring and capable of providing a total daily dosage of estrogen and progestin that is higher than that of the first vaginal ring; and a third vaginal ring capable of providing a daily dosage of estrogen that is equal to or higher than that of the second vaginal ring and capable of providing a total daily dosage of estrogen and progestin that is higher than that of the second vaginal ring; wherein the vaginal rings are capable of providing estrogen and progestin for a period of greater than 30 or 31 consecutive days.

Other aspects of the invention provide a pharmaceutical kit comprising a first vaginal ring capable of providing a daily dosage of estrogen and a daily dosage of progestin; a second vaginal ring capable of providing a total daily dosage of estrogen and progestin that is higher than that of the first vaginal ring and capable of providing a daily dosage of progestin that is less than twice that of the first vaginal ring; wherein the vaginal rings are capable of providing estrogen and progestin for a period of greater than 30 or 31 consecutive days. In some aspects of the invention, the second vaginal ring is capable of providing a daily dosage of estrogen that is equal to or higher than that of the first vaginal ring.

Some aspects of the invention provide a pharmaceutical kit comprising a first transdermal device capable of providing a daily dosage of estrogen and a daily dosage of progestin; a second transdermal device capable of providing a daily dosage of estrogen that is equal to or higher than that of the first transdermal device and capable of providing a total daily dosage of estrogen and progestin that is higher than that of the first transdermal device; and a third transdermal device capable of providing a daily dosage of estrogen that is equal to or higher than that of the second transdermal device and capable of providing a total daily dosage of estrogen and progestin that is higher than that of the second transdermal device; wherein the transdermal devices are capable of providing estrogen and progestin for a period of greater than 30 or 31 consecutive days.

Other aspects of the invention provide a pharmaceutical kit comprising a first transdermal device capable of providing a daily dosage of estrogen and a daily dosage of progestin; a second transdermal device capable of providing a total daily dosage of estrogen and progestin that is higher than that of the first transdermal device and capable of providing a daily dosage of progestin that is less than twice that of the first transdermal device; wherein the transdermal devices are capable of providing estrogen and progestin for a period of greater than 30 or 31 consecutive days. In some aspects of the invention, the second transdermal device is capable of providing a daily dosage of estrogen that is equal to or higher than that of the first transdemml device.

The pharmaceutical kits of the invention can further include instructions for proper sequential administration in accordance with the regimens of the present invention.

The present invention is also directed to a method of delivering a pharmaceutical composition for an ascending-dose extended cycle regimen of the present invention to a patient in need thereof the method comprising (a) registering in a computer readable medium the identity of a physician permitted to prescribe a pharmaceutical composition for an ascending-dose extended cycle regimen; (b) providing the patient with counseling information concerning the risks attendant to the pharmaceutical composition; (c) obtaining informed consent from the patient to receive the pharmaceutical composition despite the attendant risks; (d) registering the patient in a computer readable medium after obtaining their informed consent; and (e) permitting the patient access to the pharmaceutical composition.

The drug delivery methods of the present invention involve, inter alia, registering in a computer readable storage medium physicians who are qualified to prescribe the ascending-dose extended cycle regimen of the present invention. Once registered in the computer readable storage medium, the physician can be eligible to prescribe the pharmaceutical composition to a patient in need thereof. Generally speaking, in order to become registered in the computer readable storage medium, the physician may be required to comply with various aspects of, for example, providing patient education and counseling. The registration of the physician in the computer readable storage medium can be achieved by providing the physician, for example, by mail, facsimile transmission, or on-line transmission, with a registration card or form, preferably together with educational materials concerning the pharmaceutical composition of the present invention. The physician can complete the registration card or form by providing information requested therein, and the registration card or form can be returned to the manufacturer or distributor of the pharmaceutical composition of the present invention, or other authorized recipient of the registration materials, for example, by mail, facsimile transmission or on-line transmission. The physician's information in the registration card or form is then entered into the computer readable storage medium. Suitable computer readable storage media which can be employed for registration of the physicians (as well as patients, as discussed below) will be apparent to one of ordinary skill in the art, once in possession of the teaching of the present application.

In the course of examination of a patient, the physician may determine that the patient's condition can be improved by the administration of the pharmaceutical composition of the present invention. Prior to prescribing the pharmaceutical composition of the present invention, the physician can counsel the patient, for example, on the various risks and benefits associated with the pharmaceutical composition of the present invention. The patient can be provided full disclosure of all the known and suspected risks associated with the pharmaceutical composition of the present invention. Such counseling can be provided verbally, as well as in written form. In some embodiments, the physician can provide the patient with literature materials on the pharmaceutical composition of the present invention, such as product information, educational materials, and the like.

In addition to receiving counseling on the risks attendant to the pharmaceutical composition of the present invention, the methods of the invention further require the patient to fill out an informed consent form which is signed by the patient. Upon the completion of the informed consent form, the patient can be registered in a computer readable storage medium. The computer readable storage medium in which the patient is registered can be the same as, or different from, the computer readable storage medium in which the physician is registered.

The registration into one or more computer readable storage media of the physician and patient, according to the methods describe herein, provides a means to monitor and authorize access to the pharmaceutical composition of the present invention. Thus, the computer readable storage medium can serve to deny access to patients who fail to abide by the methods of the present invention. In some embodiments, access to the pharmaceutical composition of the present invention is in the form of a prescription, wherein the prescribing physician is registered in a computer readable storage medium, has provided counseling to the patient concerning the attendant risks of the pharmaceutical composition of the present invention, and has obtained informed consent from the patient, prior to prescribing the pharmaceutical composition of the present invention to the patient in need thereof.

All of the various aspects, embodiments and options described herein can be combined in any and all variations. The following examples are illustrative, but not limiting, of the method and compositions of the present invention. Other suitable modifications and adaptations of the variety of conditions and parameters normally encountered and obvious to those skilled in the art are within the spirit and scope of the invention. Thus, the breadth and scope of the present invention should not be limited by any of the above-described exemplary embodiments, but should be defined only in accordance with the following claims and their equivalents.

EXAMPLES

Example 1

Tables 2-6 below show examples of ascending-dose extended cycle regimens for 2-month, 3-month, 4-month, 5-month, and 6-month cycles, respectively. All regimens below comprise three phases, wherein an equivalent of 20 µg of ethinyl estradiol is administered in the first phase, 25 µg of ethinyl estradiol is administered in the second phase, and 30 µg of ethinyl estradiol is administered in the third phase. For all regimens below, an equivalent of 150 µg of levonorgestrel is administered in all three phases. For each regimen below, two possibilities are provided for phase 3, one corresponding to an allowance of 7 days of placebo following the administration of the estrogen and progestin, and the other corresponding to an allowance of 3 days of placebo following the administration of the estrogen and progestin.

TABLE 2

Two-Month Ascending-Dose Extended Cycle Regimen

| Phases | No. of days in each phase | Total estrogen dose (µg) | Total progestin dose (µg) |
| --- | --- | --- | --- |
| 1 | 14 | 280 | |
| 2 | 21 | 525 | |
| 3 (with 7 days placebo or | 14 | 420 | |
| 3 days placebo) | 18 | 540 | |
| Total | | | |
| (with 7 days placebo or | 49 (active) | 1225 | 7350 |
| 3 days placebo) | 53 (active) | 1345 | 7950 |
| Comparable Dose (2 cycles of 28-day monophasic 30 µg ethinyl estradiol oral contraceptive) | 42 active 14 placebo | 1260 | 6300 |

TABLE 3

Three-Month Ascending-Dose Extended Cycle Regimen

| Phases | No. of days in each phase | Total estrogen dose (μg) | Total progestin dose (μg) |
|---|---|---|---|
| 1 | 21 | 420 | |
| 2 | 21 | 525 | |
| 3 (with 7 days placebo or 3 days placebo) Total | 42 46 | 1260 1380 | |
| (with 7 days placebo or 3 days placebo) Comparable Dose (1 cycle of Seasonale ®; 91 days) | 84 (active) 88 (active) 84 | 2205 2325 2520 | 12600 13200 12600 |

TABLE 4

Four-Month Ascending-Dose Extended Cycle Regimen

| Phases | No. of days in each phase | Total estrogen dose (μg) | Total progestin dose (μg) |
|---|---|---|---|
| 1 | 21 | 420 | |
| 2 | 42 | 1050 | |
| 3 (with 7 days placebo or 3 days placebo) Total | 42 46 | 1260 1380 | |
| (with 7 days placebo or 3 days placebo) Comparable Dose (4 cycles of 28-day monophasic 30 μg ethinyl estradiol oral contraceptive) | 105 (active) 109 (active) 112 (84 active days) | 2730 2850 2520 | 15750 16350 12600 |

TABLE 5

Five-Month Ascending-Dose Extended Cycle Regimen

| Phases | No. of days in each phase | Total estrogen dose (μg) | Total progestin dose (μg) |
|---|---|---|---|
| 1 | 42 | 840 | |
| 2 | 49 | 1225 | |
| 3 (with 7 days placebo or 3 days placebo) Total | 42 46 | 1260 1380 | |
| (with 7 days placebo or 3 days placebo) Comparable Dose (5 cycles of 28-day monophasic 30 μg ethinyl estradiol oral contraceptive) | 133 (active) 137 (active) 140 (105 active days) | 3325 3445 3150 | 19950 20550 15750 |

TABLE 6

Six-Month Ascending-Dose Extended Cycle Regimen

| Phases | No. of days in each phase | Total estrogen dose (μg) | Total progestin dose (μg) |
|---|---|---|---|
| 1 | 42 | 840 | |
| 2 | 63 | 1575 | |

TABLE 6-continued

Six-Month Ascending-Dose Extended Cycle Regimen

| Phases | No. of days in each phase | Total estrogen dose (μg) | Total progestin dose (μg) |
|---|---|---|---|
| 3 (with 7 days placebo or 3 days placebo) Total | 70 74 | 2100 2220 | |
| (with 7 days placebo or 3 days placebo) Comparable Dose (2 cycle of Seasonale ®; 91 days) | 175 (active) 179 (active) 168 (active) | 4515 4635 5040 | 26250 26850 25200 |

TABLE 7

One-Year Ascending-Dose Extended Cycle Regimen

| Phases | No. of days in each phase | Total estrogen dose (μg) | Total progestin dose (μg) |
|---|---|---|---|
| 1 | 56 | 1120 | |
| 2 | 175 | 4375 | |
| 3 (with 7 days placebo or 3 days placebo) Total | 126 130 | 3780 3900 | |
| (with 7 days placebo or 3 days placebo) | 357 (active) 361 (active) | 9275 9395 | 53550 54150 |

Example 2

A clinical study is contemplated, as follows, using ascending-dose extended cycle regimens in accordance with the present invention.

The primary objective of this study is to evaluate and compare bleeding patterns and hormone-related symptoms in women receiving one of the following three different ascending dose extended cycle (91-day) oral contraceptive regimens, each having combination active tablets containing ethinyl estradiol (EE) and levonorgestrel (LNG), followed by EE tablets during the seven-day interval between each 84-day cycle of combination therapy:

Regimen I: Subjects will utilize a regimen of 42 days combination active tablets (20 μg EE/150 μg LNG) followed by 21 days combination active tablets (25 μg EE/150 μg LNG) followed by 21 days combination active tablets (30 μg EE/150 μg LNG) followed by 7 days of 10 μg EE tablets for two consecutive 91-day cycles.

Regimen II: Subjects will utilize a regimen of 21 days combination active tablets (20 μg EE/150 μg LNG) followed by 42 days combination active tablets (25 μg EE/150 μg LNG) followed by 21 days combination active tablets (30 μg EE/150 μg LNG) followed by 7 days of 10 μg EE tablets for two consecutive 91-day cycles.

Regimen III: Subjects will utilize a regimen of 21 days combination active tablets (20 μg EE/150 μg LNG) followed by 21 days combination active tablets (25 μg EE/150 μg LNG) followed by 42 days combination active tablets (30 μg EE/150 μg LNG) followed by 7 days of 10 μg EE tablets for two consecutive 91-day cycles.

The duration of the study is approximately 9 months, depending on where the subject is in her cycle at the time of screening. A conventional 28-day cycle contraceptive regimen, such as Portia® (Barr Laboratories, Inc., Woodcliff Lake, N.J.) can be used prior to administering the ascending-dose extended cycle regimens of the present invention.

The ascending-dose extended cycle regimens will be administered for two consecutive 91-day extended cycles (26 weeks). There will be 9 study visits, which will include a screening visit, a run-in visit, a randomization visit, five study visits occurring every 4-6 weeks during the 26 week treatment period (weeks 4, 10, 16, 22, and 26), and a final study visit occurring 14-21 clays after completion of study medication Application of the compounds, compositions and methods of the present invention for the medical or pharmaceutical uses described can be accomplished by any clinical, medical, and pharmaceutical methods and techniques as are presently or prospectively known to those skilled in the art. It will therefore be appreciated that the various embodiments which have been described above are intended to illustrate the invention and various changes and modifications can be made in the invention method without departing from the spirit or scope thereof.

Having now fully described this invention, it will be understood to those of ordinary skill in the art that the same can be performed within a wide and equivalent range of conditions, compositions, and other parameters without affecting the scope of the invention or any embodiments thereof. All patents, patent applications, and publications cited herein are fully incorporated by reference herein in their entirety.

What is claimed is:

1. A method of contraception, the method comprising:
   administering to a female in need thereof a dosage comprising estrogen and progestin for a period of 83 to 89 consecutive days,
   wherein the dosage comprising estrogen and progestin is administered in at least three phases,
   wherein the daily dosage of estrogen in the first phase is equivalent to 15 µg to 25 µg of ethinyl estradiol, the daily dosage of estrogen in the second phase is equivalent to 20 µg to 30 µg of ethinyl estradiol, and the daily dosage of estrogen in the third phase is equivalent to 25 µg to 35 µg of ethinyl estradiol,
   wherein the daily dosage of estrogen in the second phase is higher than the daily dosage of estrogen in the first phase, and
   wherein the daily dosage of estrogen in the third phase is higher than the daily dosage of estrogen in the second phase.

2. The method of claim 1, wherein the daily dosage of progestin in each of the three phases is equivalent to 100 µg to 150 µg levonorgestrel.

3. The method of claim 1, wherein the progestin is selected from the group consisting of levonorgestrel, norethindrone, norethindrone acetate, desogestrel, gestodene, dienogest, norgestimate, cyproterone acetate, norelgestromin, etonogestrel, progesterone, ethynodiol diacetate, norgestrel, trimegestone, medroxyprogesterone acetate, chlormadinone acetate, drospirenone, and esters, conjugates, and prodrugs thereof.

4. The method of claim 1, wherein the estrogen is selected from the group consisting of ethinyl estradiol, estradiol, estradiol acetate, estradiol valerate, mestranol, and esters, conjugates, and prodrugs thereof.

5. The method of claim 1, further comprising administering to the female a daily dosage consisting essentially of estrogen for a period of 2 to 8 consecutive days following the administration of the dosage comprising estrogen and progestin for 83 to 89 consecutive days.

6. The method of claim 5, wherein the daily dosage of estrogen that is administered for a period of 2 to 8 consecutive days is 5 µg to 30 µg of ethinyl estradiol.

7. The method of claim 5, further comprising administering an additional active agent that is administered (i) in combination with the dosage consisting essentially of estrogen for a period of 2 to 8 consecutive days following the administration of the dosage comprising estrogen and progestin for 83 to 89 consecutive days, (ii) continuously, (iii) intermittently, (iv) one time, or (v) once weekly.

8. The method of claim 1, wherein the female is also treated for acne, headache or pelvic pain.

9. The method of claim 1, wherein the first phase is 35 to 49 days, the second phase is 14 to 28 days, and the third phase is 14 to 32 days.

10. The method of claim 9, wherein the first phase is 42 days, the second phase is 21 days, and the third phase is 21 days.

11. The method of claim 10,
    wherein the daily dosage of estrogen in the first phase is 20 µg of ethinyl estradiol, the daily dosage of estrogen in the second phase is 25 µg of ethinyl estradiol, and the daily dosage of estrogen in the third phase is 30 µg of ethinyl estradiol, and
    wherein the daily dosage of progestin in each of the three phases is 150 µg of levonorgestrel.

12. The method of claim 11, further comprising administering to the female a daily dosage consisting essentially of 10 µg of ethinyl estradiol for 7 consecutive days following the administration of the dosage comprising estrogen and progestin.

13. The method of claim 1, wherein the first phase is 14 to 28 days, the second phase is 35 to 49 days, and the third phase is 14 to 32 days.

14. The method of claim 13, wherein the first phase is 21 days, the second phase is 42 days, and the third phase is 21 days.

15. The method of claim 14,
    wherein the daily dosage of estrogen in the first phase is 20 µg of ethinyl estradiol, the daily dosage of estrogen in the second phase is 25 µg of ethinyl estradiol, and the daily dosage of estrogen in the third phase is 30 µg of ethinyl estradiol, and
    wherein the daily dosage of progestin in each of the three phases is 150 µg of levonorgestrel.

16. The method of claim 15, further comprising administering to the female a daily dosage consisting essentially of 10 µg of ethinyl estradiol for 7 consecutive days following the administration of the dosage comprising estrogen and progestin.

17. The method of claim 1, wherein the first phase is 14 to 28 days, the second phase is 14 to 28 days, and the third phase is 35 to 53 days.

18. The method of claim 17, wherein the first phase is 21 days, the second phase is 21 days, and the third phase is 42 days.

19. The method of claim 18,
    wherein the daily dosage of estrogen in the first phase is 20 µg of ethinyl estradiol, the daily dosage of estrogen in the second phase is 25 µg of ethinyl estradiol, and the daily dosage of estrogen in the third phase is 30 µg of ethinyl estradiol, and
    wherein the daily dosage of progestin in each of the three phases is 150 µg of levonorgestrel.

20. The method of claim 19, further comprising administering to the female a daily dosage consisting essentially of 10 µg of ethinyl estradiol for 7 consecutive days following the administration of the dosage comprising estrogen and progestin.

* * * * *